(12) United States Patent
Olsen et al.

(10) Patent No.: US 9,155,877 B2
(45) Date of Patent: Oct. 13, 2015

(54) LEAD ELECTRODE FOR USE IN AN MRI-SAFE IMPLANTABLE MEDICAL DEVICE

(75) Inventors: James M. Olsen, Plymouth, MN (US); Stephen L. Bolea, Watertown, MN (US); Gregory A. Hrdlicka, Plymouth, MN (US); Carl D. Wahlstrand, Lino Lakes, MN (US); Thomas Barry Hoegh, Edina, MN (US)

(73) Assignee: MEDTRONIC, INC., Minneapolis, MN (US)

( * ) Notice: Subject to any disclaimer, the term of this patent is extended or adjusted under 35 U.S.C. 154(b) by 2206 days.

(21) Appl. No.: 11/067,024

(22) Filed: Feb. 25, 2005

(65) Prior Publication Data
US 2005/0222659 A1    Oct. 6, 2005

Related U.S. Application Data

(60) Provisional application No. 60/557,991, filed on Mar. 30, 2004.

(51) Int. Cl.
*A61N 1/08* (2006.01)
*A61N 1/05* (2006.01)
*A61N 1/37* (2006.01)

(52) U.S. Cl.
CPC .................. *A61N 1/05* (2013.01); *A61N 1/3718* (2013.01); *A61N 2001/086* (2013.01)

(58) Field of Classification Search
CPC .................................................... A61N 1/3718
USPC .................. 600/14, 300, 423; 607/9, 116
See application file for complete search history.

(56) References Cited

U.S. PATENT DOCUMENTS

| 3,788,329 | A | 1/1974 | Friedman |
| 3,915,174 | A | 10/1975 | Preston |
| 4,038,990 | A | 8/1977 | Thompson |
| 4,220,813 | A | 9/1980 | Kyle |
| 4,280,507 | A | 7/1981 | Rosenberg |
| 4,320,763 | A | 3/1982 | Money |
| 4,383,225 | A | 5/1983 | Mayer |

(Continued)

FOREIGN PATENT DOCUMENTS

| EP | 0624383 | 11/1994 |
| EP | 0 713 714 A3 | 5/1996 |

(Continued)

OTHER PUBLICATIONS

Baker, K. et al.; "Neurostimulation Systems: Assessment of Magnetic Field Interactions, Associated with 1.5- and 3-Tesla MR Systems":, 2004 Annual Meeting of the Int'l Soci . . . .

(Continued)

*Primary Examiner* — Christopher D Koharski
*Assistant Examiner* — Michael D Abreu
(74) *Attorney, Agent, or Firm* — Withers & Keys, LLC

(57) ABSTRACT

A lead configured to be implanted into a patient's body comprises a lead body and a conductive filer positioned within the lead body and having a distal portion. An electrode is electrically coupled to the lead body and comprises a stimulation portion, a bobbin, and at least one coil of wire wound on the bobbin and electrically coupled between the stimulation portion and the distal end region to form an inductor between the distal end region and the stimulation portion.

10 Claims, 12 Drawing Sheets

(56) References Cited

U.S. PATENT DOCUMENTS

| | | | |
|---|---|---|---|
| 4,628,942 A | 12/1986 | Sweeney et al. | |
| 4,711,027 A | 12/1987 | Harris | |
| 4,726,379 A | 2/1988 | Altman et al. | |
| 4,852,585 A | 8/1989 | Heath | |
| 4,920,980 A | 5/1990 | Jackowski | |
| 4,947,866 A | 8/1990 | Lessar et al. | |
| 4,951,672 A | 8/1990 | Buchwald et al. | |
| 4,991,583 A | 2/1991 | Silvian | |
| 5,012,045 A | 4/1991 | Sato | |
| 5,018,523 A | 5/1991 | Bach, Jr. et al. | |
| 5,020,544 A | 6/1991 | Dahl et al. | |
| 5,020,545 A * | 6/1991 | Soukup | 607/127 |
| 5,036,862 A | 8/1991 | Pohndorf | |
| 5,040,544 A | 8/1991 | Lessar et al. | |
| 5,063,932 A | 11/1991 | Dahl et al. | |
| 5,197,468 A | 3/1993 | Proctor et al. | |
| 5,217,010 A | 6/1993 | Tsitlik et al. | |
| 5,231,078 A * | 7/1993 | Riebman et al. | 505/192 |
| 5,246,438 A | 9/1993 | Langberg | |
| 5,260,128 A | 11/1993 | Ishii et al. | |
| 5,271,417 A | 12/1993 | Swanson et al. | |
| 5,314,459 A | 5/1994 | Swanson et al. | |
| 5,323,776 A | 6/1994 | Blakeley et al. | |
| 5,335,657 A | 8/1994 | Terry, Jr. et al. | |
| 5,349,133 A | 9/1994 | Rogers | |
| 5,366,496 A | 11/1994 | Dahl et al. | |
| 5,370,644 A | 12/1994 | Langberg | |
| 5,374,778 A | 12/1994 | Hashimoto et al. | |
| 5,417,719 A | 5/1995 | Hull et al. | |
| 5,458,629 A | 10/1995 | Baudino et al. | |
| 5,466,252 A | 11/1995 | Soukup et al. | |
| 5,476,496 A | 12/1995 | Strandberg et al. | |
| 5,504,274 A | 4/1996 | McCabe et al. | |
| 5,514,172 A | 5/1996 | Mueller | |
| 5,515,848 A | 5/1996 | Corbett, III et al. | |
| 5,523,578 A | 6/1996 | Herskovic | |
| 5,527,348 A | 6/1996 | Winkler | |
| 5,591,218 A | 1/1997 | Jacobson | |
| 5,594,304 A | 1/1997 | Graber | |
| 5,609,622 A | 3/1997 | Soukup et al. | |
| 5,629,622 A | 5/1997 | Scampini | |
| 5,649,965 A | 7/1997 | Pons et al. | |
| 5,662,697 A | 9/1997 | Li et al. | |
| 5,676,694 A | 10/1997 | Boser et al. | |
| 5,683,435 A | 11/1997 | Truex et al. | |
| 5,697,909 A | 12/1997 | Eggers et al. | |
| 5,697,958 A | 12/1997 | Paul et al. | |
| 5,702,437 A | 12/1997 | Baudino | |
| 5,722,998 A | 3/1998 | Prutchi et al. | |
| 5,727,552 A * | 3/1998 | Ryan | 600/407 |
| 5,751,539 A | 5/1998 | Stevenson et al. | |
| 5,782,241 A | 7/1998 | Felblinger et al. | |
| 5,814,076 A | 9/1998 | Brownlee | |
| 5,827,997 A | 10/1998 | Chung et al. | |
| 5,830,136 A | 11/1998 | Delonzor et al. | |
| 5,842,966 A | 12/1998 | Markoll | |
| 5,851,226 A | 12/1998 | Skubitz et al. | |
| 5,905,627 A | 5/1999 | Brendel et al. | |
| 5,927,345 A | 7/1999 | Samson | |
| 5,954,760 A | 9/1999 | Jarl | |
| 5,964,705 A | 10/1999 | Truwit et al. | |
| 5,970,429 A | 10/1999 | Martin | |
| 6,033,408 A | 3/2000 | Gage et al. | |
| 6,055,457 A | 4/2000 | Bonner | |
| 6,101,417 A | 8/2000 | Vogel et al. | |
| 6,195,267 B1 | 2/2001 | MacDonald et al. | |
| 6,198,972 B1 | 3/2001 | Hartlaub et al. | |
| 6,209,764 B1 | 4/2001 | Hartlaub et al. | |
| 6,258,071 B1 | 7/2001 | Brookes | |
| 6,265,466 B1 | 7/2001 | Glatkowski | |
| 6,284,971 B1 | 9/2001 | Atalar et al. | |
| 6,302,740 B1 | 10/2001 | Holmstrom | |
| 6,348,070 B1 | 2/2002 | Teissl et al. | |
| 6,424,234 B1 | 7/2002 | Stevenson | |
| 6,471,699 B1 | 10/2002 | Fleischman et al. | |
| 6,488,704 B1 | 12/2002 | Connelly et al. | |
| 6,494,916 B1 | 12/2002 | Babalola et al. | |
| 6,501,991 B1 | 12/2002 | Honeck et al. | |
| 6,503,648 B1 | 1/2003 | Wang | |
| 6,506,972 B1 | 1/2003 | Wang | |
| 6,529,774 B1 | 3/2003 | Greene | |
| 6,538,191 B1 | 3/2003 | MacDonald | |
| 6,640,137 B2 | 10/2003 | MacDonald | |
| 6,660,116 B2 | 12/2003 | Wolf et al. | |
| 6,673,999 B1 | 1/2004 | Wang et al. | |
| 6,675,033 B1 | 1/2004 | Lardo et al. | |
| 6,689,835 B2 | 2/2004 | Amarasekera et al. | |
| 6,695,761 B2 | 2/2004 | Oschman et al. | |
| 6,708,051 B1 | 3/2004 | Durousseau | |
| 6,711,440 B2 | 3/2004 | Deal et al. | |
| 6,713,671 B1 | 3/2004 | Wang et al. | |
| 6,718,203 B2 | 4/2004 | Weiner et al. | |
| 6,718,207 B2 | 4/2004 | Connelly | |
| 6,725,092 B2 | 4/2004 | MacDonald et al. | |
| 6,741,892 B1 | 5/2004 | Meadows et al. | |
| 6,750,055 B1 | 6/2004 | Connelly et al. | |
| 6,757,566 B2 | 6/2004 | Weiner et al. | |
| 6,760,628 B2 | 7/2004 | Weiner et al. | |
| 6,763,268 B2 | 7/2004 | MacDonald et al. | |
| 6,765,144 B1 | 7/2004 | Wang et al. | |
| 6,768,053 B1 | 7/2004 | Wang et al. | |
| 6,778,856 B2 | 8/2004 | Connelly et al. | |
| 6,792,316 B2 | 9/2004 | Sass | |
| 6,793,642 B2 | 9/2004 | Connelly et al. | |
| 6,795,730 B2 | 9/2004 | Connelly et al. | |
| 6,795,736 B2 | 9/2004 | Connelly et al. | |
| 6,815,609 B1 | 11/2004 | Wang et al. | |
| 6,844,492 B1 | 1/2005 | Wang et al. | |
| 6,845,267 B2 | 1/2005 | Harrison et al. | |
| 6,864,418 B2 | 3/2005 | Wang et al. | |
| 6,869,683 B2 | 3/2005 | Sakurai et al. | |
| 6,872,882 B2 | 3/2005 | Fritz | |
| 6,879,861 B2 | 4/2005 | Benz et al. | |
| 6,882,519 B2 | 4/2005 | Uzawa et al. | |
| 6,895,280 B2 | 5/2005 | Meadows et al. | |
| 6,901,290 B2 | 5/2005 | Foster et al. | |
| 6,906,256 B1 | 6/2005 | Wang | |
| 6,920,361 B2 | 7/2005 | Williams | |
| 6,922,590 B1 | 7/2005 | Whitehurst | |
| 6,930,242 B1 | 8/2005 | Helfer | |
| 6,949,929 B2 * | 9/2005 | Gray et al. | 324/318 |
| 6,971,391 B1 | 12/2005 | Wang et al. | |
| 6,980,865 B1 | 12/2005 | Wang et al. | |
| 6,982,378 B2 | 1/2006 | Dickson | |
| 6,999,818 B2 * | 2/2006 | Stevenson et al. | 607/37 |
| 6,999,821 B2 | 2/2006 | Jenney et al. | |
| 7,015,393 B2 | 3/2006 | Weiner | |
| 7,103,413 B2 | 9/2006 | Swanson | |
| 7,118,693 B2 | 10/2006 | Glatkowski et al. | |
| 7,123,013 B2 | 10/2006 | Gray | |
| 7,162,302 B2 | 1/2007 | Wang et al. | |
| 7,174,219 B2 | 2/2007 | Wahlstrand et al. | |
| 7,233,825 B2 | 6/2007 | Jorgenson et al. | |
| 7,257,449 B2 | 8/2007 | Bodner | |
| 7,282,260 B2 | 10/2007 | LeGrande et al. | |
| 7,292,894 B2 | 11/2007 | Belden | |
| 7,319,901 B2 | 1/2008 | Dublin | |
| 7,363,090 B2 | 4/2008 | Halperin | |
| 7,389,148 B1 | 6/2008 | Morgan | |
| 7,591,831 B2 | 9/2009 | Parsonage et al. | |
| 2002/0032468 A1 | 3/2002 | Hill et al. | |
| 2002/0038135 A1 | 3/2002 | Connelly et al. | |
| 2002/0116028 A1 | 8/2002 | Greatbatch et al. | |
| 2002/0116029 A1 | 8/2002 | Miller et al. | |
| 2002/0116033 A1 | 8/2002 | Greatbatch et al. | |
| 2002/0116034 A1 | 8/2002 | Miller et al. | |
| 2002/0128689 A1 | 9/2002 | Connelly et al. | |
| 2002/0128691 A1 | 9/2002 | Connelly | |
| 2002/0133086 A1 | 9/2002 | Connelly et al. | |
| 2002/0133199 A1 | 9/2002 | MacDonald et al. | |
| 2002/0133200 A1 | 9/2002 | Weiner et al. | |
| 2002/0133201 A1 | 9/2002 | Connelly et al. | |
| 2002/0133202 A1 | 9/2002 | Connelly et al. | |
| 2002/0133208 A1 | 9/2002 | Connelly | |

(56) References Cited

U.S. PATENT DOCUMENTS

| | | |
|---|---|---|
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0183740 A1 | 12/2002 | Edwards et al. |
| 2002/0188345 A1 | 12/2002 | Pacetti |
| 2003/0009207 A1 | 1/2003 | Paspa et al. |
| 2003/0014080 A1 | 1/2003 | Baudino |
| 2003/0036776 A1 | 2/2003 | Foster et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0109901 A1 | 6/2003 | Greatbatch |
| 2003/0117787 A1 | 6/2003 | Nakauchi |
| 2003/0120148 A1 | 6/2003 | Pacetti |
| 2003/0120197 A1 | 6/2003 | Kaneko et al. |
| 2003/0135114 A1 | 7/2003 | Pacetti et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144716 A1 | 7/2003 | Reinke et al. |
| 2003/0144717 A1 | 7/2003 | Hegele |
| 2003/0144718 A1 | 7/2003 | Zeijlemaker |
| 2003/0144719 A1 | 7/2003 | Zeijlemaker |
| 2003/0144720 A1* | 7/2003 | Villaseca et al. ............ 607/122 |
| 2003/0144721 A1 | 7/2003 | Villaseca et al. |
| 2003/0204217 A1 | 10/2003 | Greatbatch |
| 2003/0225331 A1 | 12/2003 | Diederich et al. |
| 2004/0020674 A1 | 2/2004 | Fadden et al. |
| 2004/0068307 A1 | 4/2004 | Goble |
| 2004/0199069 A1 | 10/2004 | Connelly et al. |
| 2004/0263174 A1 | 12/2004 | Gray et al. |
| 2005/0065587 A1 | 3/2005 | Gryzwa |
| 2005/0070972 A1 | 3/2005 | Wahlstrand |
| 2005/0080471 A1 | 4/2005 | Chitre et al. |
| 2005/0113876 A1 | 5/2005 | Weiner |
| 2005/0159661 A1 | 7/2005 | Connelly et al. |
| 2005/0182471 A1 | 8/2005 | Wang |
| 2005/0222642 A1 | 10/2005 | Przybyszewski |
| 2005/0222656 A1 | 10/2005 | Wahlstrand |
| 2005/0222657 A1 | 10/2005 | Wahlstrand |
| 2005/0222658 A1 | 10/2005 | Hoegh et al. |
| 2006/0155270 A1 | 7/2006 | Hancock |
| 2006/0200218 A1 | 9/2006 | Wahlstrand |
| 2006/0247747 A1 | 11/2006 | Olsen |
| 2006/0247748 A1 | 11/2006 | Wahlstrand |
| 2007/0106332 A1 | 5/2007 | Demker |
| 2007/0185556 A1 | 8/2007 | Williams |
| 2008/0033497 A1 | 2/2008 | Bulkes |
| 2008/0039709 A1 | 2/2008 | Karmakar |
| 2008/0195186 A1 | 8/2008 | Li |
| 2008/0195187 A1 | 8/2008 | Li |
| 2008/0269863 A1 | 10/2008 | Alexander |

FOREIGN PATENT DOCUMENTS

| | | |
|---|---|---|
| EP | 0 760 196 B1 | 3/1997 |
| EP | 1 273 922 A1 | 1/2003 |
| EP | 1424095 | 6/2004 |
| EP | 1466576 | 10/2004 |
| JP | 07/255863 | 10/1995 |
| JP | 11/086641 | 3/1999 |
| WO | WO96/28951 | 9/1996 |
| WO | WO 97/41923 | 11/1997 |
| WO | WO 99/10035 | 3/1999 |
| WO | WO 99/19020 | 4/1999 |
| WO | WO 99/60370 | 11/1999 |
| WO | WO 00/27279 | 5/2000 |
| WO | WO01/80940 | 11/2001 |
| WO | WO02/083236 | 10/2002 |
| WO | WO 03/037429 A1 | 5/2003 |
| WO | WO03/061755 | 7/2003 |
| WO | WO03/063946 | 8/2003 |
| WO | WO 03/063948 A3 | 8/2003 |
| WO | WO 03/063952 A3 | 8/2003 |
| WO | WO 03/063953 A3 | 8/2003 |
| WO | WO03/063954 | 8/2003 |
| WO | WO 03/063955 A1 | 8/2003 |
| WO | WO 03/063956 A2 | 8/2003 |
| WO | WO 03/063957 A3 | 8/2003 |
| WO | WO 03/075797 A3 | 9/2003 |
| WO | WO 03/092326 A1 | 11/2003 |
| WO | WO 03/095022 A2 | 11/2003 |
| WO | WO 2004/052448 A1 | 6/2004 |
| WO | WO 2004/073040 A3 | 8/2004 |
| WO | WO2005/030322 | 4/2005 |
| WO | WO2005/102444 | 11/2005 |
| WO | WO2005/102445 | 11/2005 |
| WO | WO2005/102446 | 11/2005 |
| WO | WO2005/102447 | 11/2005 |
| WO | WO2006/031317 | 3/2006 |
| WO | WO 2006/031317 A2 | 3/2006 |
| WO | WO2006/093685 | 9/2006 |
| WO | WO2006/093686 | 9/2006 |
| WO | WO2006/118640 | 11/2006 |
| WO | WO2006/118641 | 11/2006 |
| WO | WO2008/100839 | 8/2008 |
| WO | WO2008/100840 | 8/2008 |
| WO | WO2008/134196 | 11/2008 |

OTHER PUBLICATIONS

Finelli, D. et al.; "MR Imaging-Related Heating of Deep Brain Stimulation Electrodes: In Vitro Study"; AJNR AM J Neuroadiol 23:1, Nov./Dec. 2002.

Baker, K. et al.; "Evaluation of Specific Absorption Rate as a Dosimeter of MRI-Related Implant Heating"; Journal of Magnetic Resonance Imaging 20:315-320 (2004).

Rezai, A. et al.; "Neurostimulation System Used for Deep Brain Stimulation (DBS): MR Safety Issues and Implications of Failing to Follow Safety Recommendations" Investigati . . . .

Rezai, A. et al.; "Neurostimulation Systems for Deep Brain Stimulation In Vitro Evaluation of Magnetic Resonance Imaging-Related Heating at 1.5 Tesla"; Journal of Magnetic . . . .

Medtronic Activa Product Family and Procedure Solution Brochure.

Medtronic Neurostimulation Systems Brochure.

Chung, D.D.L., "Carbon Fiber Composites", 1994, chapter 1, p. 8, table 1.2, Elsevier, ISBN: 978-0-7506-9169-7.

Chung, D.D.L., Comparison of Submicron-Diameter Carbon Filaments and Conventional Carbon Fibers as Fillers in Composite Materials, Carbon 39 (2001) pp. 1119-1125, Elsevier Science Ltd.

Chung, D.D.L., Electromagnetic Interference Shielding Effectiveness of Carbon Materials Carbon 29 (2001) pp. 279-285, Elsevier Science Ltd.

International Search Report for PCT/US04/031638.
International Search Report for PCT/US04/040082.
International Search Report for PCT/US04/041201.
International Search Report for PCT/US04/042081.
International Search Report for PCT/US05/000322.
International Search Report for PCT/US06/005535.
International Search Report for PCT/US08/053540.
International Search Report for PCT/US08/053541.
International Search Report for PCT/US08/059358.
International Search Report for PCT/US06/005539.
International Search Report for PCT/US06/006754.
International Search Report for PCT/US06/006755.

Jou, W.S. "A Novel Structure of Woven Continuous-Carbon Fiber Composites with High Electromagnetic Shielding", Journal of Electronic Materials, vol. 33, No. 3, Mar. 1, 2004, pp. 162-170(9), Minerals, Metals and Materials Society, http://findarticles.com/p/articles/mi_qu3776/is_200403/ai_n9405_582/print.

Kolin, et al., "An Electromagnetic Catheter Flow Meter for Determination of Blood Flow in Major Arteries," Department of Biophysics, Physiology, and Radiology, University of California School of Medicine (Los Angeles) Jan. 19, 1988, Proc. N.A.S. vol. 59, pp. 808-815.

(56) References Cited

OTHER PUBLICATIONS

Kolin, et al., "An Electromagnetic intravascular Blood-Flow Sensor", Department of Biophysics, University of California School of Medicine (Los Angeles), Mar. 20, 1967, Proc. N.A.S., vol. 57, pp. 1331-1337.

Kolin, et al., "Miniaturization of the Electromagnetic Blood Flow Meter and Its Use for the Recording of Circulatory Responses of Conscious Animals to Sensory Stimuli", Department of Biophysics, University of California at Los Angeles, Aug. 1959, Proc. N.A.S. vol. 45(8), pp. 1312-1321.

Quick et al., "Endourethral MRI", Magnetic Resonance in Medicine, 45:138-446, 2001.

U.S. Appl. No. 10/945,739 non-final office action dated Aug. 23, 2006.

U.S. Appl. No. 10/945,739 response to non-final office action dated Aug. 23, 2006.

U.S. Appl. No. 10/945,739: non-final office action dated Feb. 20, 2007.

U.S. Appl. No. 10/945,739: response to non-final dated Feb. 20, 2007.

U.S. Appl. No. 10/945,739: non-final office action dated Dec. 6, 2007.

U.S. Appl. No. 10/945,739: response to non-final office action dated Dec. 6, 2007.

U.S. Appl. No. 10/945,739: final office action dated May 1, 2008.

U.S. Appl. No. 10/945,739: RCE and response to final office action dated May 1, 2008.

U.S. Appl. No. 10/945,739: corrected amendment dated May 23, 2008.

U.S. Appl. No. 10/945,739: advisory action dated Jul. 28, 2008.

U.S. Appl. No. 10/945,739: non-final office action dated Aug. 19, 2008.

U.S. Appl. No. 10/945,739: response to non-final office action dated Aug. 19, 2008.

U.S. Appl. No. 10/945,739: final office action dated May 22, 2009.

U.S. Appl. No. 10/945,739: RCE and response to final office action dated May 22, 2009.

U.S. Appl. No. 10/945,739: non-final office action dated Sep. 28, 2009.

U.S. Appl. No. 10/945,739: response to non-final office action dated Sep. 28, 2009.

U.S. Appl. No. 10/946,968: non-final office action dated Aug. 29. 2006.

U.S. Appl. No. 10/946,968: response to non-final office action dated Aug. 29, 2006.

U.S. Appl. No. 10/946,968: final rejection dated Apr. 20, 2007.

U.S. Appl. No. 10/981,092: restriction requirement dated Aug. 25, 2006.

U.S. Appl. No. 10/981,092: response to restriction requirement dated Aug. 25, 2006.

U.S. Appl. No. 10/993,195: restriction requirement dated Oct. 27, 2006.

U.S. Appl. No. 10/993,195: response to restriction requirement dated Oct. 27, 2006.

U.S. Appl. No. 10/993,195: non-final office action dated Dec. 6, 2006.

U.S. Appl. No. 10/993,195: response to non-final office action dated Dec. 6, 2006.

U.S. Appl. No. 10/993,195: final office action dated May 8, 2007.

U.S. Appl. No. 10/993,195: response to final office action dated May 8, 2007.

U.S. Appl. No. 10/993,195: non-final office action dated Jul. 26, 2007.

U.S. Appl. No. 10/993,195: response to non-final office action dated Jul. 26, 2007.

U.S. Appl. No. 10/993,195: non-final office action dated May 30, 2008.

U.S. Appl. No. 10/993,195: response to non-final office action dated May 30, 2008.

U.S. Appl. No. 10/993,195: non-final office action dated Feb. 25, 2009.

U.S. Appl. No. 10/993,195: response to non-final office action dated Feb. 25, 2009.

U.S. Appl. No. 10/993,195: final office action dated Oct. 6, 2009.

U.S. Appl. No. 10/993,195: response to final office action dated Oct. 6, 2009.

U.S. Appl. No. 10/993,195: advisory action dated Dec. 18, 2009.

U.S. Appl. No. 10/993,195: pre-appeal brief dated Feb. 5, 2010.

U.S. Appl. No. 10/993,195: panel decision dated Mar. 10, 2010.

U.S. Appl. No. 11/009,862: restriction requirement dated Aug. 8, 2007.

U.S. Appl. No. 11/009,862: response to restriction requirement dated Aug. 8, 2007.

U.S. Appl. No. 11/009,862: non-final office action dated Oct. 2, 2007.

U.S. Appl. No. 11/009,862: response to non-final office action dated Oct. 2, 2007.

U.S. Appl. No. 11/009,862: final office action dated May 22, 2008.

U.S. Appl. No. 11/009,862: RCE and response to final office action dated May 22, 2008.

U.S. Appl. No. 11/009,862: non-final office action dated Oct. 27, 2008.

U.S. Appl. No. 11/009,862: response to non-final office action dated Oct. 27, 2008.

U.S. Appl. No. 11/009,862: final office action dated Apr. 9, 2009.

U.S. Appl. No. 11/009,862: RCE and response to final office action dated Apr. 9, 2009.

U.S. Appl. No. 11/009,862: non-final office action dated Aug. 3, 2009.

U.S. Appl. No. 11/009,862: response to non-final office action dated Aug. 3, 2009.

U.S. Appl. No. 11/009,862: final office action dated Feb. 25, 2010.

U.S. Appl. No. 11/009,862: RCE and response to final office action dated Feb. 25, 2010.

U.S. Appl. No. 11/071,136: non-final office action dated Feb. 23, 2007.

U.S. Appl. No. 11/071,136: response to non-final office action dated Feb. 23, 2007.

U.S. Appl. No. 11/071,136: final office action dated Aug. 1, 2007.

U.S. Appl. No. 11/071,136: response to final office action dated Aug. 1, 2007.

U.S. Appl. No. 11/071,136: non-final office action dated Oct. 19, 2007.

U.S. Appl. No. 11/071,136: response to non-final office action dated Oct. 19, 2007.

U.S. Appl. No. 11/071,136: final office action dated May 14, 2008.

U.S. Appl. No. 11/071,136: RCE and response to final office action dated May 14, 2008.

U.S. Appl. No. 11/071,136: restriction requirement dated Oct. 31, 2008.

U.S. Appl. No. 11/071,136: response to restriction requirement dated Oct. 31, 2008.

U.S. Appl. No. 11/071,136: non-final office action dated Feb. 13, 2009.

U.S. Appl. No. 11/071,136: response to non-final office action dated Feb. 13, 2009.

U.S. Appl. No. 11/071,136: final office action dated Feb. 19, 2010.

U.S. Appl. No. 11/071,136: RCE and response to final office action dated Feb. 19, 2010.

U.S. Appl. No. 11/117,882: non-final office action dated Feb. 20, 2008.

U.S. Appl. No. 11/117,882: response to non-final office action dated Feb. 20, 2008.

U.S. Appl. No. 11/117,882: final office action dated Aug. 26, 2008.

U.S. Appl. No. 11/117,882: RCE and response to final office action dated Aug. 26, 2008.

U.S. Appl. No. 11/117,882: non-final office action dated Mar. 23, 2009.

U.S. Appl. No. 11/117,882: response to non-final office action dated Mar. 23, 2009.

U.S. Appl. No. 11/117,882: final office action dated Oct. 21, 2009.

U.S. Appl. No. 11/117,882: RCE and response to final office action dated Oct. 21, 2009.

(56) References Cited

OTHER PUBLICATIONS

U.S. Appl. No. 11/117,882: non-final office action dated Mar. 1, 2010.
U.S. Appl. No. 11/117,882: response to non-final office action dated Mar. 1, 2010.
U.S. Appl. No. 11/117,894: non-final office action dated Dec. 11, 2007.
U.S. Appl. No. 11/117,894: response to non-final office action dated Dec. 11, 2007.
U.S. Appl. No. 11/117,894: final office action dated May 2, 2008.
U.S. Appl. No. 11/117,894: RCE and response to final office action dated May 2, 2008.
U.S. Appl. No. 11/117,894: non-final office action dated Dec. 2, 2008.
U.S. Appl. No. 11/117,894: response to non-final office action dated Dec. 2. 2008.
U.S. Appl. No. 11/117,894: final office action dated May 28, 2009.
U.S. Appl. No. 11/117,894: RCE and response to final office action dated May 28, 2009.
U.S. Appl. No. 11/117,894: restriction requirement dated Nov. 24, 2009.
U.S. Appl. No. 11/117,894: response to restriction requirement dated Nov. 24, 2009.
U.S. Appl. No. 11/117,894: non-final office action dated Mar. 31, 2010.
U.S. Appl. No. 11/117,894: response to non-final office action dated Mar. 31, 2010.
U.S. Appl. No. 11/346,486: restriction requirement dated Aug. 6, 2008.
U.S. Appl. No. 11/346,486: response to restriction requirement dated Aug. 6, 2008.
U.S. Appl. No. 11/346,486: non-final office action dated Sep. 26, 2008.
U.S. Appl. No. 11/346,486: response to non-final office action dated Sep. 26, 2008.
U.S. Appl. No. 11/346,486: non-final office action dated Apr. 2, 2009.
U.S. Appl. No. 11/346,486: response to non-final office action dated Apr. 2, 2009.
U.S. Appl. No. 11/346,486: final office action dated Jan. 12, 2010.
U.S. Appl. No. 11/346,486: RCE and response to final office action dated Jan. 12, 2010.
U.S. Appl. No. 11/674,992: non-final office action dated Mar. 19, 2009.
U.S. Appl. No. 11/674,992: response to non-final office action dated Mar. 19, 2009.
U.S. Appl. No. 11/674,992: final office action dated Oct. 29, 2009.
U.S. Appl. No. 11/674,992: RCE and response to final office action dated Oct. 29, 2009.
U.S. Appl. No. 11/674,995: non-final office action dated Mar. 19, 2009.
U.S. Appl. No. 11/674,995: response to non-final office action dated Mar. 19, 2009.
U.S. Appl. No. 11/674,995: final office action dated Oct. 29, 2009.
U.S. Appl. No. 11/674,995: RCE and response to final office action dated Oct. 29, 2009.
U.S. Appl. No. 11/739,787: non-final office action dated Jun. 12, 2009.
U.S. Appl. No. 11/739,787: response to non-final office action dated Jun. 12, 2009.
U.S. Appl. No. 11/739,787: non-final office action dated Jan. 11, 2010.
U.S. Appl. No. 11/739,787: response to non-final office action dated Jan. 11, 2010.
U.S. Appl. No. 11/739,787: final office action dated May 13, 2010.
U.S. Appl. No. 11/739,787: response to final office action dated May 13, 2010.
PCT/US04/42081: search report and written opinion dated Mar. 14, 2005.
PCT/US04/42081: response to written opinion dated Mar. 14, 2005.
PCT/US04/42081: second written opinion dated Mar. 10, 2006.
PCT/US04/42081: response to second written opinion dated Mar. 10, 2006.
PCT/US04/42081: IPRP.
PCT/US06/05539: search report and written opinion dated Feb. 15, 2006.
PCT/US06/05539: response to written opinion dated Feb. 15, 2006.
PCT/US06/05539: IPRP dated Jun. 28, 2007.
PCT/US06/06754: search report and written opinion dated Jul. 24, 2006.
PCT/US06/06754: response to written opinion dated Jul. 24 2006.
PCT/US06/06754: IPRP dated Jun. 2, 2007.
PCT/US06/06755: search report and written opinion dated Jul. 24, 2006.
PCT/US06/06755: response to written opinion dated Jul. 24, 2006.
PCT/US06/06755: IPRP dated Aug. 21, 2007.
PCT/US08/53540: search report and written opinion dated Jul. 17, 2008.
PCT/US08/53540: IPRP dated Aug. 27, 2009.
PCT/US08/53541: search report and written opinion dated Jun. 27, 2008.
PCT/US08/59358: search report and written opinion dated Jul. 14, 2008.
PCT/US04/31638: search report and written opinion dated Jan. 17, 2005.
PCT/US04/31638: IPRP dated Apr. 6, 2006.
PCT/US04/40082: search report and written opinion dated Mar. 15, 2005.
PCT/US04/40082: response to written opinion dated Mar. 15, 2005.
PCT/US04/40082: IPRP dated Mar. 5, 2006.
PCT/US04/041201: search report and written opinion dated Mar. 16, 2005.
PCT/US05/00322: search report and written opinion dated Mar. 30, 2005.
PCT/US05/00322: response to written opinion dated Mar. 30, 2005.
PCT/US05/00322: second written opinion dated Apr. 18, 2006.
PCT/US05/00322: response to second written opinion dated Apr. 18, 2006.
PCT/US05/00322: IPRP dated Jul. 5, 2006.
PCT/US06/05535: search report and written opinion dated May 31, 2006.
PCT/US06/05535: IPRP dated Sep. 7, 2007.

* cited by examiner

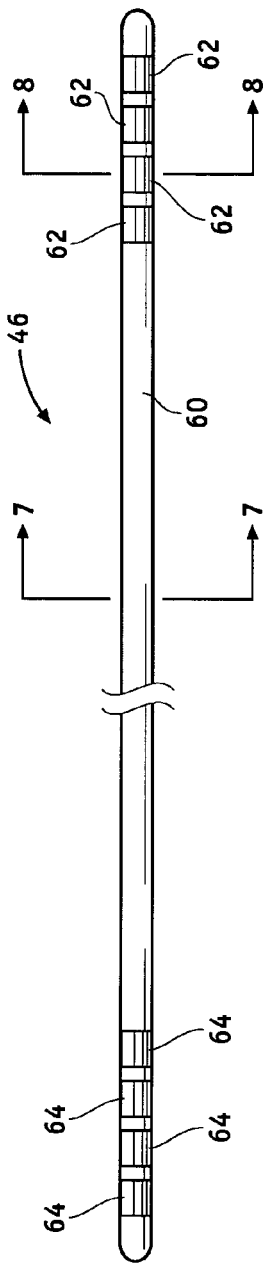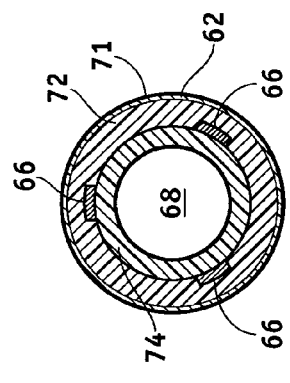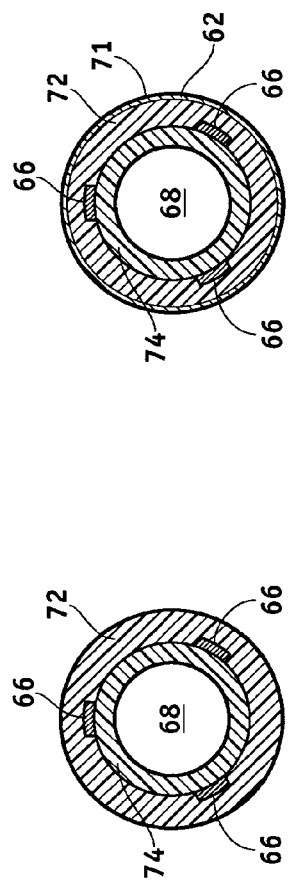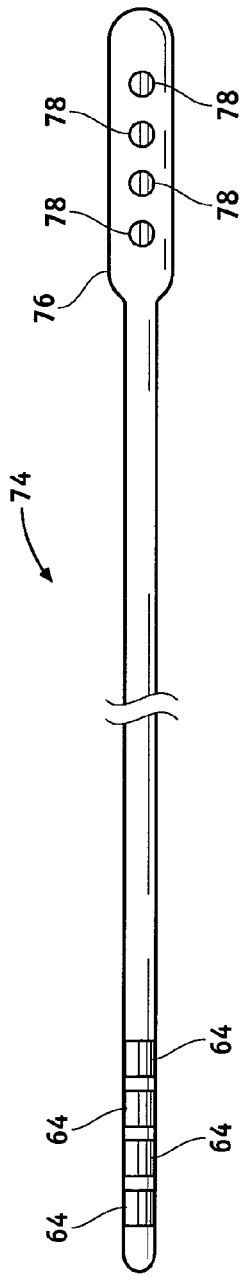

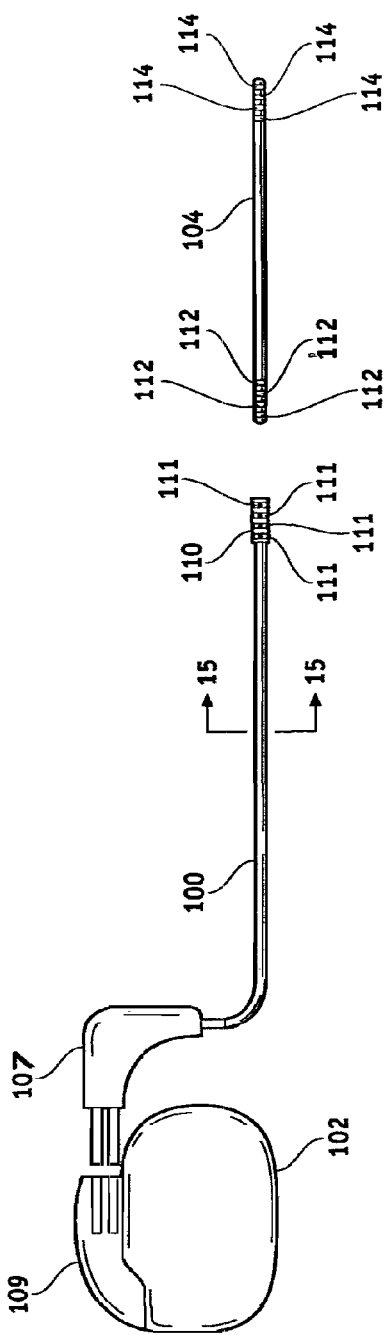
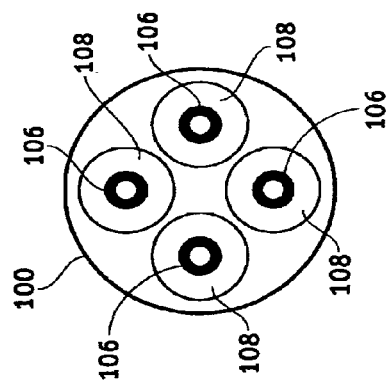
FIG. 14
FIG. 15

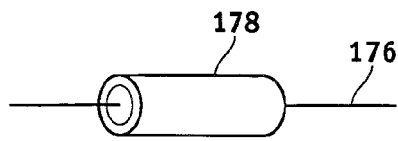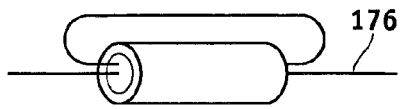
FIG. 33  FIG. 34
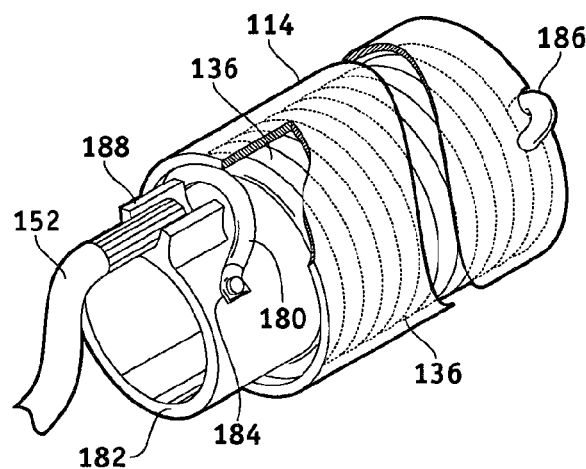
FIG. 35
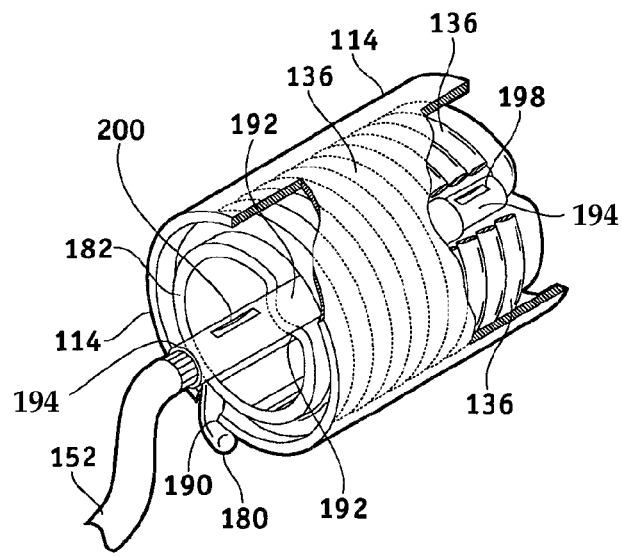
FIG. 36

LEAD ELECTRODE FOR USE IN AN MRI-SAFE IMPLANTABLE MEDICAL DEVICE

CROSS-REFERENCES TO RELATED APPLICATIONS

This application claims the benefit of U.S. Provisional Application No. 60/557,991, filed Mar. 30, 2004.

FIELD OF THE INVENTION

The present invention generally relates to implantable medical devices, and more particularly to an implantable MRI-safe lead of the type which includes a stimulation electrode and wherein a RF choke is utilized in conjunction with the stimulation electrode to assist in managing the energy induced in the lead during a MRI scan so as to reduce undesirable heating at the electrode.

BACKGROUND OF THE INVENTION

Implantable medical devices are commonly used today to treat patients suffering from various ailments. Such implantable devices may be utilized to treat conditions such as pain, incontinence, sleep disorders, and movement disorders such as Parkinson's disease and epilepsy. Such therapies also appear promising in the treatment of a variety of psychological, emotional, and other physiological conditions.

One known type of implantable medical device, a neurostimulator, delivers mild electrical impulses to neural tissue using an electrical lead. For example, to treat pain, electrical impulses may be directed to specific sites. Such neurostimulation may result in effective pain relief and a reduction in the use of pain medications and/or repeat surgeries.

Typically, such devices are totally implantable and may be controlled by a physician or a patient through the use of an external programmer. Current systems generally include a non-rechargeable primary cell neurostimulator, a lead extension, and a stimulation lead, and the two main classes of systems may be referred to as: (1) Spinal Cord Stimulation (SCS) and (2) Deep Brain Stimulation (DBS).

An SCS stimulator may be implanted in the abdomen, upper buttock, or pectoral region of a patient and may include at least one extension running from the neurostimulator to the lead or leads which are placed somewhere along the spinal cord. Each of the leads (to be discussed in detail hereinbelow) currently contains from one to eight electrodes. Each extension (likewise to be discussed in detail below) is plugged into or connected to the neurostimulator at a proximal end thereof and is coupled to and interfaces with the lead or leads at a distal end of the extension.

The implanted neurostimulation system is configured to send mild electrical pulses to the spinal cord. These electrical pulses are delivered through the lead or leads to regions near the spinal cord or a nerve selected for stimulation. Each lead includes a small insulated wire coupled to an electrode at the distal end thereof through which the electrical stimulation is delivered. Typically, the lead also comprises a corresponding number of internal wires to provide separate electrical connection to each electrode such that each electrode may be selectively used to provide stimulation. Connection of the lead to an extension may be accomplished by means of a connector block including, for example, a series or combination of set screws, ball seals, etc. The leads are inserted into metal set screw bocks, and the metal set screws are manipulated to press the contacts against the blocks to clamp them in place and provide electrical connection between the lead wires and the blocks. Such an arrangement is shown in U.S. Pat. No. 5,458,629 issued Oct. 17, 1995 and entitled "Implantable Lead Ring Electrode and Method of Making".

A DBS system comprises similar components (i.e. a neurostimulator, at least one extension, and at least one stimulation lead) and may be utilized to provide a variety of different types of electrical stimulation to reduce the occurrence or effects of Parkinson's disease, epileptic seizures, or other undesirable neurological events. In this case, the neurostimulator may be implanted into the pectoral region of the patient. The extension or extensions may extend up through the patient's neck, and the leads/electrodes are implanted in the brain. The leads may interface with the extension just above the ear on both sides of the patient. The distal end of the lead may contain from four to eight electrodes and, as was the case previously, the proximal end of the lead may be connected to the distal end of the extension and may be held in place by set screws. The proximal portion of the extension plugs into the connector block of the neurostimulator.

Magnetic resonance imaging (MRI) is a relatively new and efficient technique that may be used in the diagnosis of many neurological disorders. It is an anatomical imaging tool which utilizes non-ionizing radiation (i.e. no x-rays or gamma rays) and provides a non-invasive method for the examination of internal structure and function. For example, MRI permits the study of the overall function of the heart in three dimensions significantly better than any other imaging method. Furthermore, imaging with tagging permits the non-invasive study of regional ventricular function.

MRI scanning is widely used in the diagnosis of injuries to the head. In fact, the MRI is now considered by many to be the preferred standard of care, and failure to prescribe MRI scanning can be considered questionable. Approximately sixteen million MRIs were performed in 1996, followed by approximately twenty million in the year 2000. It is projected that forty million MRIs will be performed in 2004.

In an MRI scanner, a magnet creates a strong magnetic field which aligns the protons of hydrogen atoms in the body and then exposes them to radio frequency (RF) energy from a transmitter portion of the scanner. This spins the various protons, and they produce a faint signal that is detected by a receiver portion of the scanner. A computer renders these signals into an image. During this process, three electromagnetic fields are produced; i.e. (1) a static magnetic field, (2) a gradient magnetic field, and (3) a radio frequency (RF) magnetic field. The main or static magnetic field may typically vary between 0.2 and 3.0 Tesla. A nominal value of 1.5 Tesla is approximately equal to 15,000 Gauss which is 30,000 times greater than the Earth's magnetic field of approximately 0.5 Gauss. The time varying or gradient magnetic field may have a maximum strength of approximately 40 milli-Tesla/meters at a frequency of 0-5 KHz. The RF may, for example, produce thousands of watts at frequencies of between 8-215 MHz. For example, up to 20,000 watts may be produced at 64 MHz and a static magnetic field of 1.5 Tesla; that is, 20 times more power than a typical toaster. Thus, questions have arisen regarding the potential risk associated with undesirable interaction between the MRI environment and the above-described neurostimulation systems; e.g. forces and torque on the implantable device within the MRI scanner caused by the static magnetic field, RF-induced heating, induced currents due to gradient magnetic fields, device damage, and image distortion. Of these interactions, the problems associated with induced RF currents in the leads are most deserving of attention since it has been found that the temperature in the leads can rise by as much as 25° Centigrade or higher in an MRI environment.

A similar problem occurs when a patient undergoes diathermy treatment employing RF energy to create eddy currents in the patient's tissue so as to heat the tissue and promote healing. In this environment, current may also be produced in the implanted lead causing undesirable heating of the electrodes as described above.

Accordingly, it would be desirable to provide an implantable medical device that may be safely operated in an MRI environment. It would be further desirable to provide an implantable medical device such as a SCS or DBS neurostimulation system that may be operated in an MRI environment without the generation of significant undesirable heat in the leads due to induced RF currents. It would be further desirable to provide an MRI-safe, implantable lead that may be used in conjunction with known implantable medical devices wherein RF chokes reduce the energy induced in lead electrode during an MRI scan thereby reducing the generation of unwanted heat at the leads stimulation electrodes. Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

According to a broad aspect of the invention, there is provided a lead configured to be implanted into a patient's body, comprising a lead body, a conductive filer is positioned within the lead body and having a distal portion. An electrode is electrically coupled to the lead body and comprises a stimulation portion; a bobbin, and at least one coil of wire wound on the bobbin and electrically coupled between the stimulation portion and the distal end region to form an inductor between the distal end region and the stimulation portion.

BRIEF DESCRIPTION OF THE DRAWINGS

The present invention will hereinafter be described in conjunction with the following drawing figures, wherein like numerals denote like elements, and:

FIG. 6 is a top view of the lead shown in FIG. 2;

FIGS. 7 and 8 are cross-sectional views taken along lines 7-7 and 8-8, respectively, in FIG. 6;

FIG. 9 is a top view of an alternate lead configuration;

FIG. 14 is an exploded view of a neurostimulation system;

FIG. 15 is a cross-sectional view of the extension shown in FIG. 14 taken along line 15-15;

FIGS. 33 and 34 illustrate additional embodiments of the present invention utilizing ferrite beads; and FIGS. 35 and 36 illustrate still further embodiments of the present invention.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Figure 1:
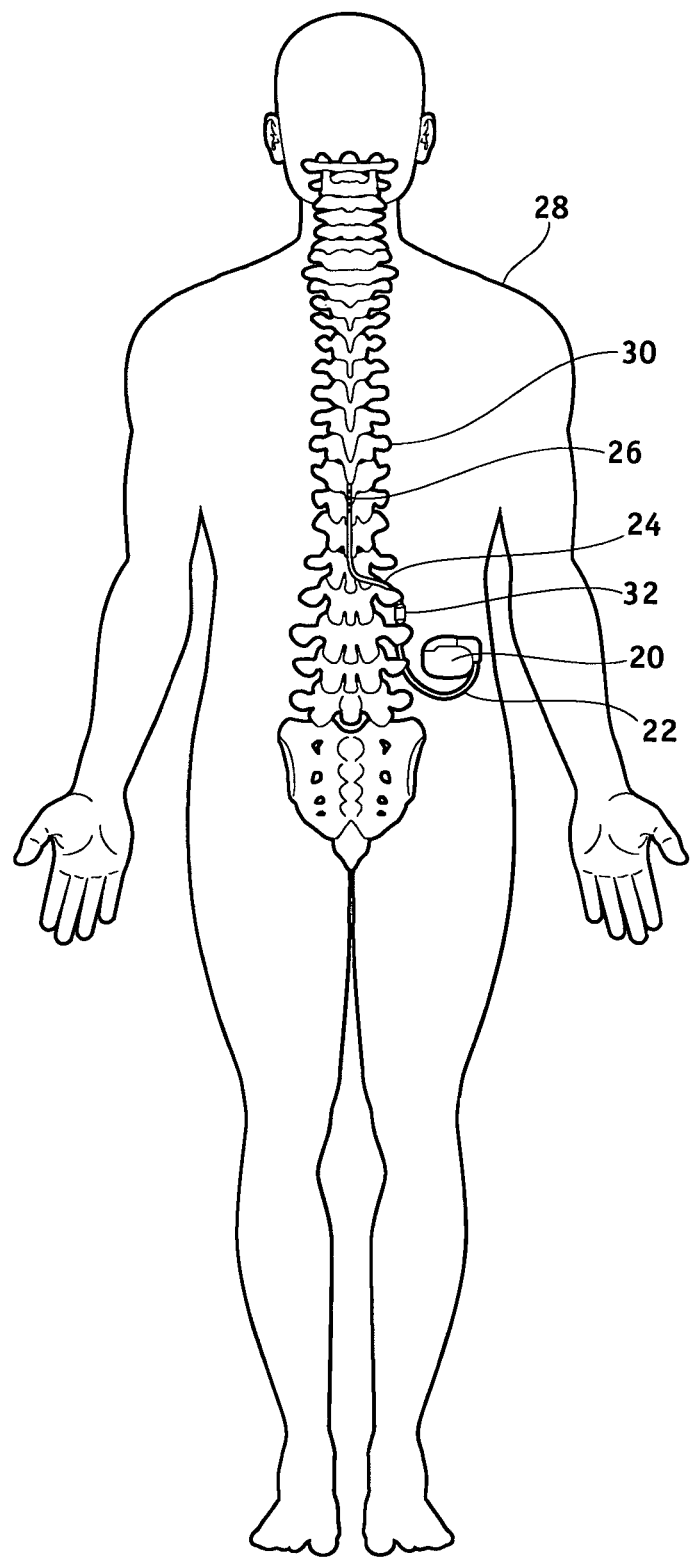
FIG. 1 illustrates a typical spinal cord stimulation system implanted in a patient.

FIG. 1 illustrates a typical SCS system implanted in a patient. As can be seen, the system comprises a pulse generator such as an SCS neurostimulator 20, a lead extension 22 having a proximal end coupled to neurostimulator 20 as will be more fully described below, and a lead 24 having proximal end coupled to the distal end of extension 22 and having a distal end coupled to one or more electrodes 26. Neurostimulator 20 is typically placed in the abdomen of a patient 28, and lead 24 is placed somewhere along spinal cord 30. As stated previously, neurostimulator 20 may have one or two leads each having four to eight electrodes. Such a system may also include a physician programmer and a patient programmer (not shown). Neurostimulator 20 may be considered to be an implantable pulse generator of the type available from Medtronic, Inc. and capable of generating multiple pulses occurring either simultaneously or one pulse shifting in time with respect to the other, and having independently varying amplitudes and pulse widths. Neurostimulator 20 contains a power source and the electronics for sending precise, electrical pulses to the spinal cord to provide the desired treatment therapy. While neurostimulator 20 typically provides electrical stimulation by way of pulses, other forms of stimulation may be used as continuous electrical stimulation.

Lead 24 is a small medical wire having special insulation thereon and includes one or more insulated electrical conductors each coupled at their proximal end to a connector and to contacts/electrodes 26 at its distal end. Some leads are designed to be inserted into a patient percutaneously (e.g. the Model 3487A Pisces—Quad® lead available from Medtronic, Inc.), and some are designed to be surgically implanted (e.g. Model 3998 Specify® lead, also available form Medtronic, Inc.). Lead 24 may contain a paddle at its distant end for housing electrodes 26; e.g. a Medtronic paddle having model number 3587A. Alternatively, electrodes 26 may comprise one or more ring contacts at the distal end of lead 24 as will be more fully described below.

While lead 24 is shown as being implanted in position to stimulate a specific site in spinal cord 30, it could also be positioned along the peripheral nerve or adjacent neural tissue ganglia or may be positioned to stimulate muscle tissue. Furthermore, electrodes 26 may be epidural, intrathecal or placed into spinal cord 30 itself. Effective spinal cord stimulation may be achieved by any of these lead placements. While the lead connector at proximal end of lead 24 may be coupled directly to neurostimulator 20, the lead connector is typically coupled to lead extension 22 as is shown in FIG. 1. An example of a lead extension is Model 7495 available from Medtronic, Inc.

A physician's programmer (not shown) utilizes telemetry to communicate with the implanted neurostimulator 20 to enable the physician to program and manage a patient's therapy and troubleshoot the system. A typical physician's programmer is available from Medtronic, Inc. and bears Model No. 7432. Similarly, a patient's programmer (also not shown) also uses telemetry to communicate with neurostimulator 20 so as to enable the patient to manage some aspects of their own therapy as defined by the physician. An example of a patient programmer is Model 7434®3 EZ Patient Programmer available from Medtronic, Inc.

Implantation of a neurostimulator typically begins with the implantation of at least one stimulation lead usually while the patient is under a local anesthetic. While there are many spinal cord lead designs utilized with a number of different implantation techniques, the largest distinction between leads revolves around how they are implanted. For example, surgical leads have been shown to be highly effective, but require a laminectomy for implantation. Percutaneous leads can be introduced through a needle, a much easier procedure. To simplify the following explanation, discussion will focus on percutaneous lead designs, although it will be understood by those skilled in the art that the inventive aspects are equally applicable to surgical leads. After the lead is implanted and positioned, the lead's distal end is typically anchored to minimize movement of the lead after implantation. The lead's proximal end is typically configured to connect to a lead extension 22. The proximal end of the lead extension is then connected to the neurostimulator 20.

Figure 2:
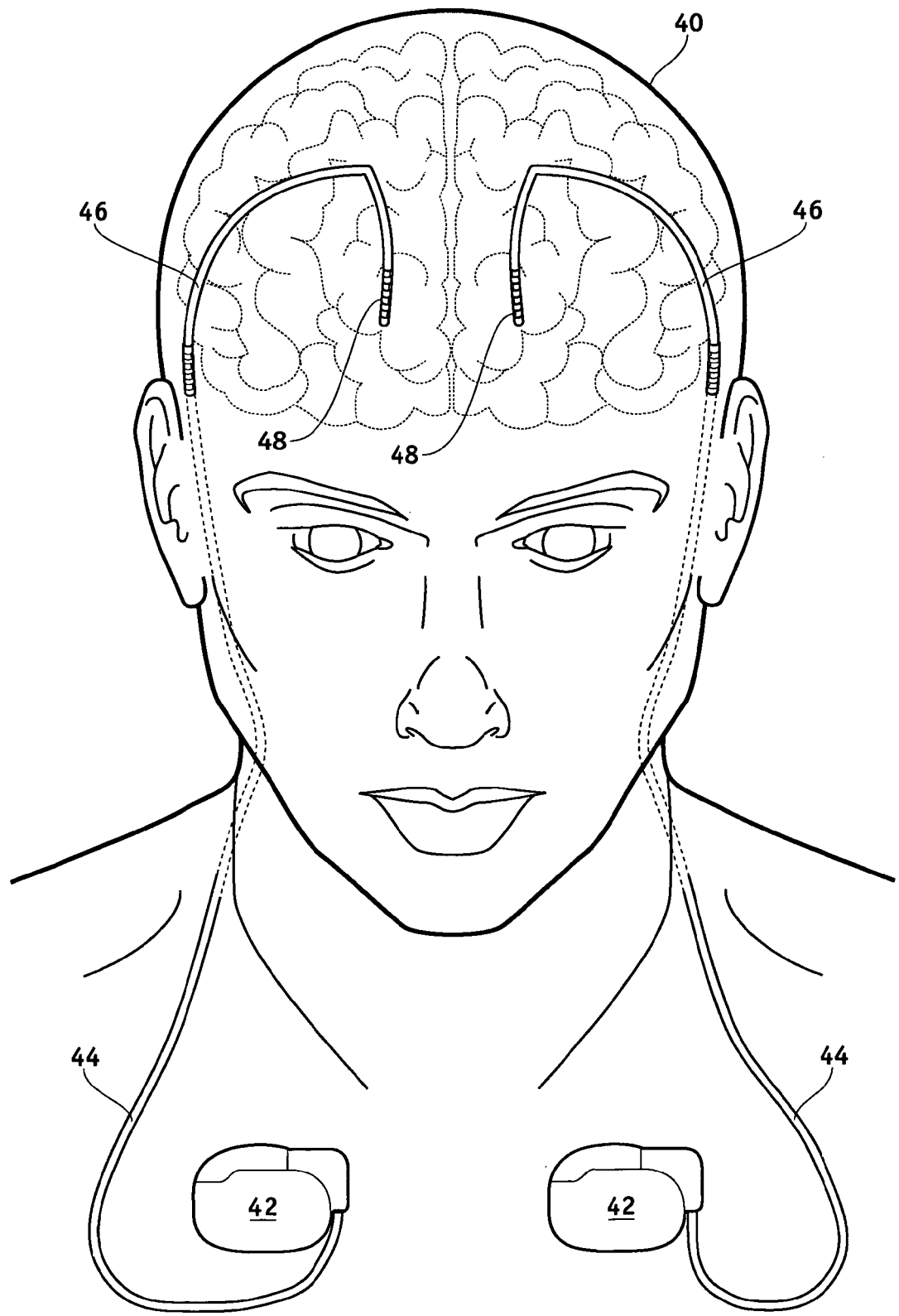
FIG. 2 illustrates a typical deep brain stimulation system implanted in a patient.

FIG. 2 illustrates a DBS system implanted in a patient 40 and comprises substantially the same components as does an SCS; that is, at least one neurostimulator, at least one extension, and at least one stimulation lead containing one or more electrodes. As can be seen, each neurostimulator 42 is implanted in the pectoral region of the patient. Extensions 44 are deployed up through the patient's neck, and leads 46 are implanted in the patient's brain as is shown at 48. As can be seen, each of the leads 46 is connected to its respective extension 44 just above the ear on both sides of patient 40.

Figure 5:
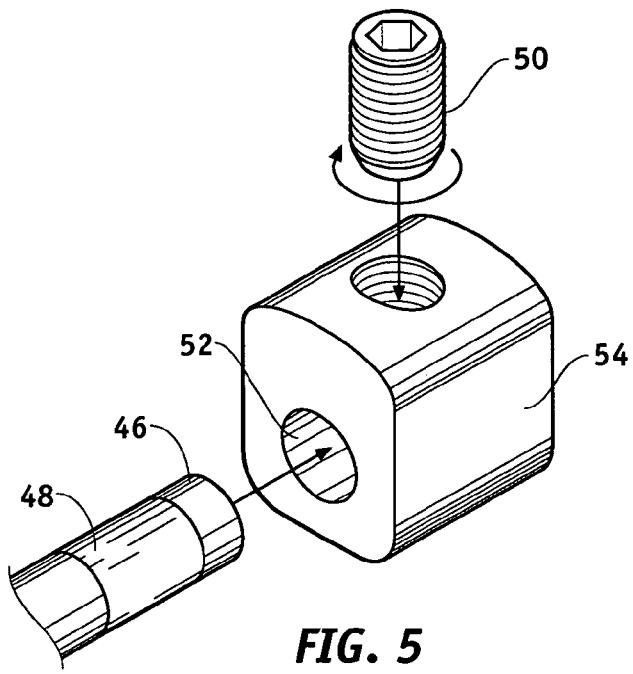
FIG. 5 is an isometric view of an example of a connector screw block suitable for connecting the lead of FIG. 3 to the extension shown in FIG. 4.
Figure 3:
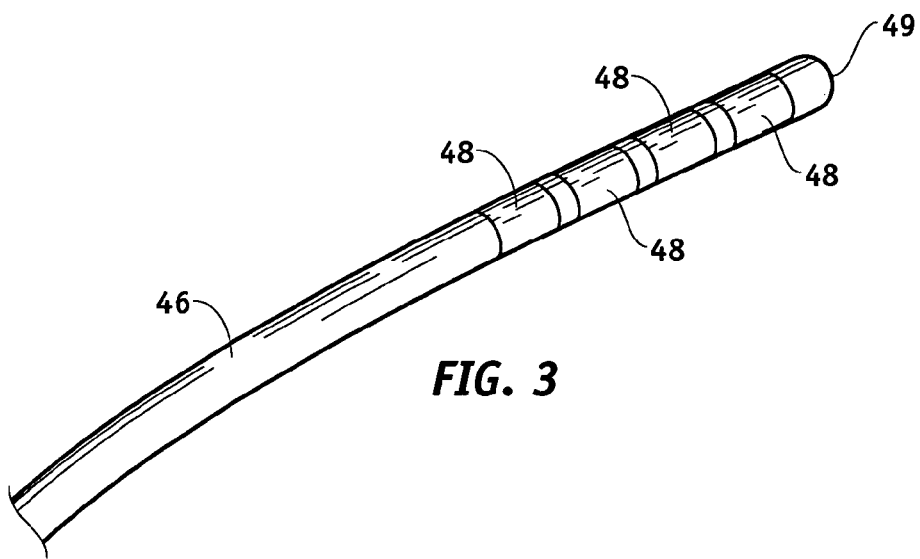
FIG. 3 is an isometric view of the distal end of the lead shown in FIG. 2.
Figure 4:
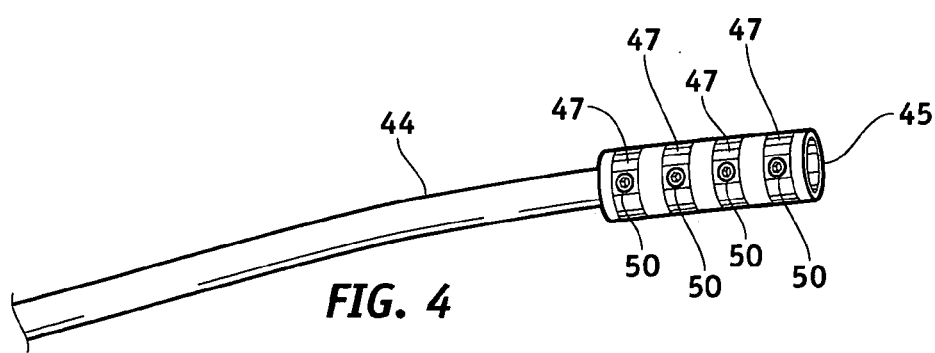
FIG. 4 is an isometric view of the distal end of the extension shown in FIG. 2.

FIG. 3 is an isometric view of the distal end of lead 46. In this case, four ring electrodes 48 are positioned on the distal end of lead 46 and coupled to internal conductors of filers (not shown) contained within lead 46. Again, while four ring electrodes are shown in FIG. 3, it is to be understood that the number of electrodes can vary to suit a particular application. FIG. 4 is an isometric view of the distal end of extension 44, which includes a connector portion 45 having four internal contacts 47. The proximal end of the DBS lead is shown in FIG. 3, plugs into the distal connector 45 of extension 44, and is held in place by means of, for example, a plurality (e.g. 4) of set screws 50. For example, referring to FIG. 5, lead 46 terminates in a series of proximal electrical ring contacts 48 (only one of which is shown in FIG. 5). Lead 46 may be inserted through an axially aligned series of openings 52 (again only one shown) in screw block 54. With a lead 46 so inserted, a series of set screws (only one shown) are screwed into block 54 to drive contacts 48 against blocks 54 and secure and electrically couple the lead 46. It should be appreciated, however, that other suitable methods for securing lead 46 to extension 44 may be employed. The proximal portion of extension 44 is secured to neurostimulator 42 as is shown in FIGS. 1 and 2.

FIG. 6 is a top view of lead 46 shown in FIG. 2. FIGS. 7 and 8 are cross-sectional views taken along lines 7-7 and 8-8, respectively, in FIG. 6. Distal end 60 of lead 46 includes at least one electrode 62 (four are shown). As stated previously, up to eight electrodes may be utilized. Each of electrodes 62 is preferably constructed as is shown in FIG. 8. That is, electrode 62 may comprise a conductive ring 71 on the outer surface of the elongate tubing making up distal shaft 60. Each electrode 62 is electrically coupled to a longitudinal wire 66 (shown in FIGS. 7 and 8) each of which extends to a contact 64 at the proximal end of lead 46. Longitudinal wires 66 may be of a variety of configurations; e.g. discreet wires, printed circuit conductors, etc. From the arrangement shown in FIG. 6, it should be clear that four conductors or filers run through the body of lead 46 to electrically connect the proximal electrodes 64 to the distal electrodes 62. As will be further discussed below, the longitudinal conductors 66 may be spirally configured along the axis of lead 46 until they reach the connector contacts.

The shaft of lead 46 preferably has a lumen 68 extending therethrough for receiving a stylet that adds a measure of rigidity during installation of the lead. The shaft preferably comprises a comparatively stiffer inner tubing member 74 (e.g. a polyamine, polyamide, high density polyethylene, polypropylene, polycarbonate or the like). Polyamide polymers are preferred. The shaft preferably includes a comparatively softer outer tubing member 72; e.g. silicon or other suitable elastomeric polymer. Conductive rings 71 are preferably of a biocompatible metal such as one selected from the noble group of metals, preferably palladium, platinum or gold and their alloys.

FIG. 9 illustrates an alternative lead 74 wherein distal end 76 is broader (e.g. paddle-shaped) to support a plurality of distal electrodes 78. A lead of this type is shown in FIG. 1. As was the case with the lead shown in FIGS. 6, 7, and 8, distal electrodes 78 are coupled to contacts 64 each respectively by means of an internal conductor or filer. A more detailed description of the leads shown in FIGS. 6 and 9 may be found in U.S. Pat. No. 6,529,774 issued Mar. 4, 2003 and entitled "Extradural Leads, Neurostimulator Assemblies, and Processes of Using Them for Somatosensory and Brain Stimulation".

Figure 11:
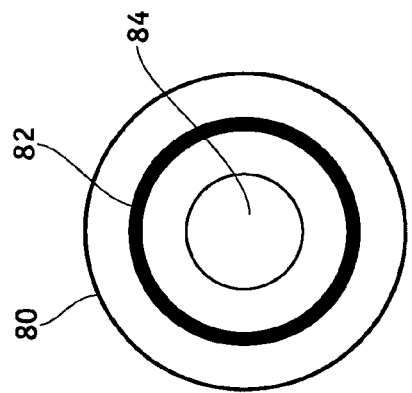
FIGS. 10 and 11 are longitudinal and radial cross-sectional views, respectively, of a helically wound lead of the type shown in FIG. 6.
Figure 10:
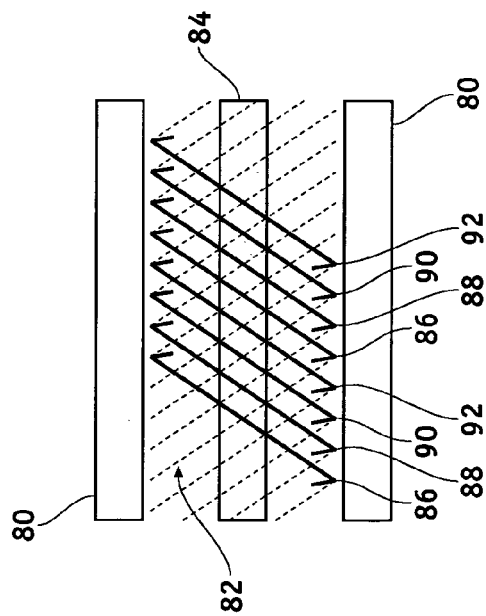

Leads of the type described above may be of the wound helix filer type or of the cabled filer type. FIGS. 10 and 11 are longitudinal and radial cross-sectional views, respectively, of a helically wound lead of the type shown in FIG. 6. The lead comprises an outer lead body 80; a plurality of helically wound, co-radial lead filers 82; and a stylet lumen 84. As stated previously, a stylet is a stiff, formable insert placed in the lead during implant so as to enable the physician to steer the lead to an appropriate location. FIG. 10 illustrates four separate, co-radially wound filers 86, 88, 90, and 92 which are electrically insulated from each other and electrically couple a single electrode 62 (FIG. 6) to a single contact 64 (FIG. 6).

Figure 13:
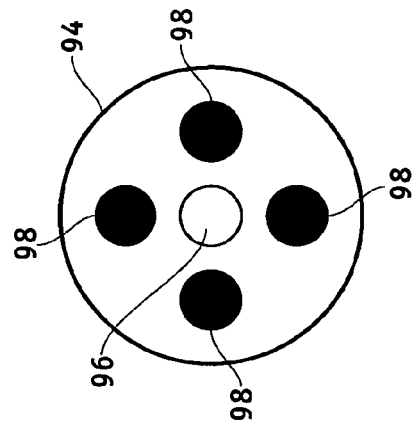
FIGS. 12 and 13 are longitudinal and radial cross-sectional views, respectively, of a cabled lead.
Figure 12:
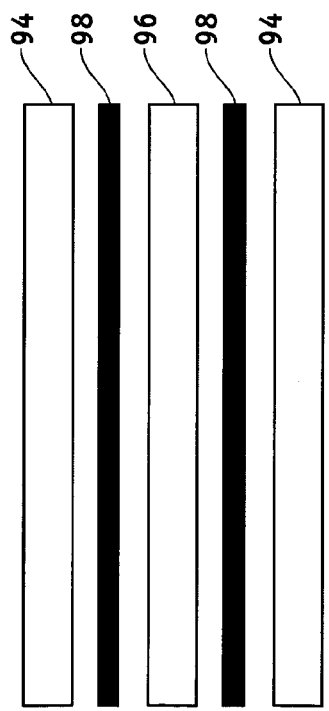

As can be seen, lead filers 82 have a specific pitch and form a helix of a specific diameter. The helix diameter is relevant in determining the inductance of the lead. These filers themselves also have a specific diameter and are made of a specific material. The filer diameter, material, pitch and helix diameter are relevant in determining the impedance of the lead. In the case of a helically wound lead, the inductance contributes to a frequency dependent impedance. FIGS. 12 and 13 are longitudinal and radially cross-sectional views, respectively, of a cabled lead. The lead comprises outer lead body 94, stylet lumen 96, and a plurality (e.g. four to eight) of straight lead filers 98. It should be understood that each straight filer 98 may, if desired, be of a cable construction comprised of a plurality of insulated straight filers; e.g. a center filer surrounded by an additional six filers.

FIG. 14 is an exploded view of a neurostimulation system that includes an extension 100 configured to be coupled between a neurostimulator 102 and lead 104. The proximal portion of extension 100 comprises a connector 107 configured to be received or plugged into connector block 109 of neurostimulator 102. The distal end of extension 100 likewise comprises a connector 110 including internal contacts 111 and is configured to receive the proximal end of lead 104 having contacts 112 thereon. The distal end of lead 104 includes distal electrodes 114.

FIG. 15 is a cross-sectional view of extension 100. Lead extension 100 has a typical diameter of 0.1 inch, which is significantly larger than that of lead 104 so as to make extension 100 more durable than lead 104. Extension 100 differs from lead 104 also in that each filer 106 in lead body is helically wound or coiled in its own lumen 108 and not co-radially wound with the rest of the filers as was the case in lead 104.

The diameter of typical percutaneous leads is approximately 0.05 inch. This diameter is based upon the diameter of the needle utilized in the surgical procedure to deploy the lead and upon other clinical anatomical requirements. The length of such percutaneous SCS leads is based upon other clinical anatomical requirements. The length of such percutaneous SCS leads is typically 28 centimeters; however, other lengths are utilized to meet particular needs of specific patients and to accommodate special implant locations.

Lead length is an important factor in determining the suitability of using the lead in an MRI environment. For example, the greater length of the lead, the larger the effective loop area that is impacted by the electromagnetic field (e.g. the longer the lead, the larger the antenna). Furthermore, depending on the lead length, there can be standing wave effects that create areas of high current along the lead body. This can be problematic if the areas of high current are near the distal electrodes.

Compared to the helically wound lead, the cable lead has smaller DC resistance because the length of the straight filer is less than that of a coiled filer and the impedance at frequency is reduced because the inductance has been significantly reduced. It has been determined that the newer cabled filer designs tend to be more problematic in an MRI environment than do the wound helix filer designs. It should be noted that straight filers for cable leads sometimes comprise braided stranded wire that includes a number of smaller strands woven to make up each filer. This being the case, the number of strands could be varied to alter the impedance.

It has been discovered that high lead impedances at MRI operational frequencies can reduce the heating of an electrode during an MRI procedure. The high impedance acts as a choke for current flowing through the lead and, by restricting this current, electrode heating can be reduced. As previously alluded to, leads have been intentionally designed with low impedance to enhance system stimulation efficiency. The simplest way to increase the impedance of a lead is to increase its DC resistance. This may be accomplished in a number of ways that may, if desired, be combined to achieve an optimal impedance.

For example, the resistance R of a lead filer is governed by the equation:

$$R = \frac{L}{\sigma a} \qquad \text{Equation (1)}$$

where R is the resistance, L is the length of the filer, σ is the conductivity, and α is the cross-sectional area. Decreasing the conductivity and/or the cross-sectional area of the filer will increase resistance proportionally. One typical lead utilizes a stainless steel (non-cored MP35N) filer having a conductivity of $1.1 \times 10^6$ mhos/meter, a diameter of approximately 0.005 inch, and a length of approximately 100 centimeters. Using Equation (1), the resistance R of the lead is approximately 71.8 ohms. If the diameter were reduced to 0.002 inch, R could be increased to approximately 448.5 ohms.

Impedance can also be obtained through inductance in accordance with the equation:

$$Z = j(2\pi f)L \qquad \text{Equation (2)}$$

where Z is the impedance, L is the inductance, and f is the frequency. Inductance L may be either distributed or discrete. For example, distributed inductance can be created by helically coiling the lead filers in such a way as to achieve the above described optimal impedance at MR frequencies. The inductance is governed by the equation:

$$L = \frac{\mu N^2 A}{l} \qquad \text{Equation (3)}$$

where N is the number of turns in the helix, A is the cross-sectional area, l is the length, and μ is the permeability.

A discrete inductor in the form of, for example, a surface-mount component or wound helix in the conductor path of the lead may be utilized to provide inductance, and therefore impedance. In this way, a frequency-dependent impedance can be added at one of more locations in the lead. One such location may be near or within the lead's distal electrode. One terminal of the inductor may be attached directly to the electrode, and the other terminal may be attached to the filer. Preferably, the choke windings should comprise a high conductivity material (e.g. silver-cored MP35n) in order to minimize heating in the choke. For example, a filer having a conductivity greater than $1.1 \times 10^6$ mhos/meter. Alternatively a choke with an inductance greater than 1 μH and a DC resistance less than 40 ohms.

There are a number of techniques that may be utilized to attach a discrete inductor to a lead electrode; e.g. welding, soldering, using a conductive epoxy, etc. It has been found that placing the inductor close to or within the distal electrode minimizes heating during an MR scan by adding a frequency dependent impedance as described above. Furthermore, an RF choke implemented near the stimulation electrodes reflects energy away from the electrodes. That is, since the impedance of the choke at high frequency is significantly higher than the rest of the lead, a standing wave sees an impedance mismatch, and a portion of the standing wave is reflected based on the magnitude of the mismatch. The higher the mismatch the greater the amount of energy reflected. For example, a typical lead has a characteristic impedance of about 100 ohms. A choke of about 1.5 µH will yield an impedance of about 600 ohms at 64 MHz, a sizable mismatch.

Figure 16:
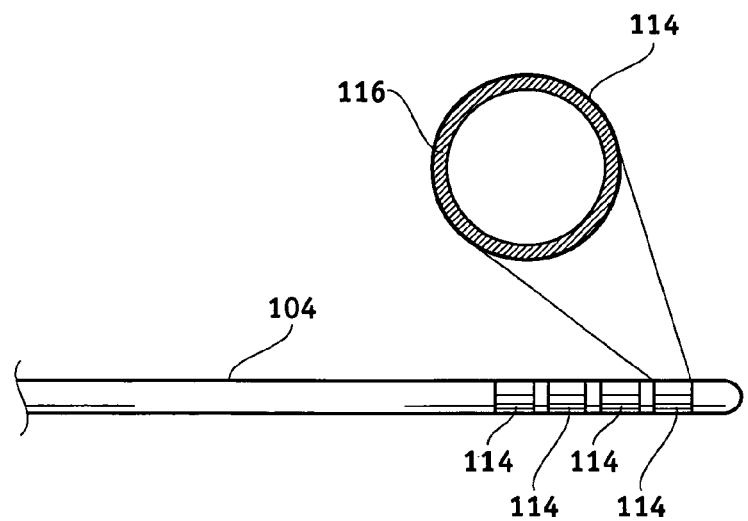
FIG. 16 illustrates a cylindrically packaged discrete inductor configured within a distal electrode.
Figure 17:
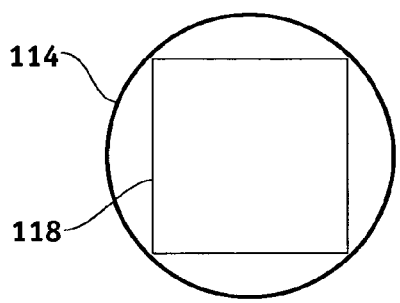
FIG. 17 is a cross-sectional view of a prismatically packaged discrete inductor configured within a distal electrode.
Figure 18:
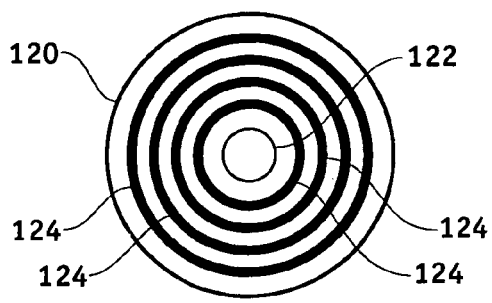
FIG. 18 is a cross-sectional view of a quadripolar coaxially-wound lead.

The discrete inductor may comprise a coil of wire of, for example, cylindrical or torroidal construction. While both may be accommodated in a cylindrical package that may fit easily inside a lead electrode, it should be clear that packages of other shapes may be accommodated. The discrete inductor is preferably placed inside a distal electrode where it will have the benefit of the mechanical protection afforded by the electrode. For example, FIG. 16 illustrates a cylindrically packaged discrete inductor 116 configured within distal electrode 114. FIG. 17 is a cross-sectional view of a prismatically packaged discrete inductor 118 configured within distal electrode 114, and FIG. 18 is a cross-sectional view of a quadripolar coaxially wound lead including outer lead body 120, stylet lumen 122, and at least four helically and coaxially wound lead filers 124. The lead shown in FIG. 18 provides for a high helix angle and lead inductances that reach or exceed 40µH/cm. Each filer 124 can be individually insulated or positioned in its own sleeve. Furthermore, each filer 124 may be wound in either direction; and for added strength, certain ones of the filers may be wound in opposite directions.

To achieve the desired impedance at MRI frequencies, a choke comprising, for example, thirty to forty coils of wire having a diameter of from 0.002 inch to 0.050 inch, may be utilized. To protect the choke having these characteristics during, for example, flexing, a bobbin may be provided that provides protection, strain relief, and a convenient mechanism for winding the coils of the inductor. The bobbin may be manufactured integrally with a stimulation electrode or may comprise a separate part that is secured to stimulation electrode by welding, soldering, or any other suitable method. If desired, the bobbin may be made of plastic or any other material that offers the required rigidity and secured to the electrode by any appropriate means.

Figure 19:
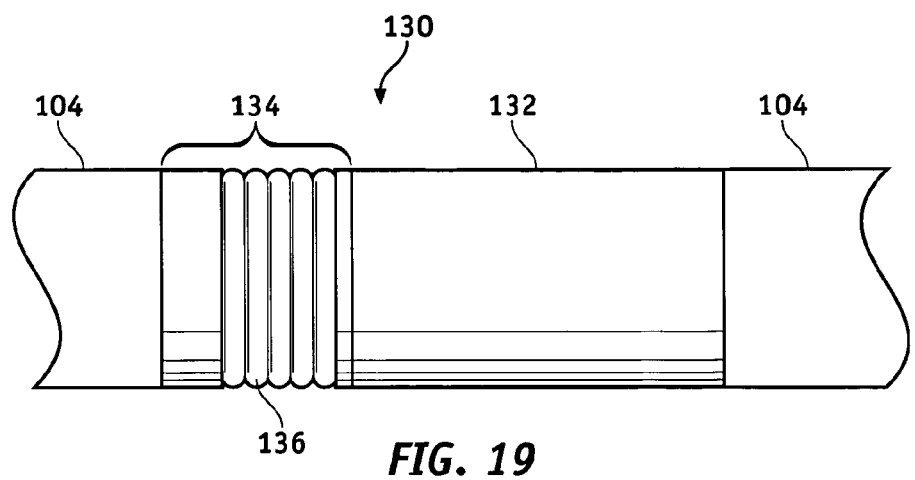
FIGS. 19, 20, and 21 are top partial cross-sectional, and isometric views, respectively, of a stimulation lead including a stimulation electrode/inductor assembly.
Figure 20:
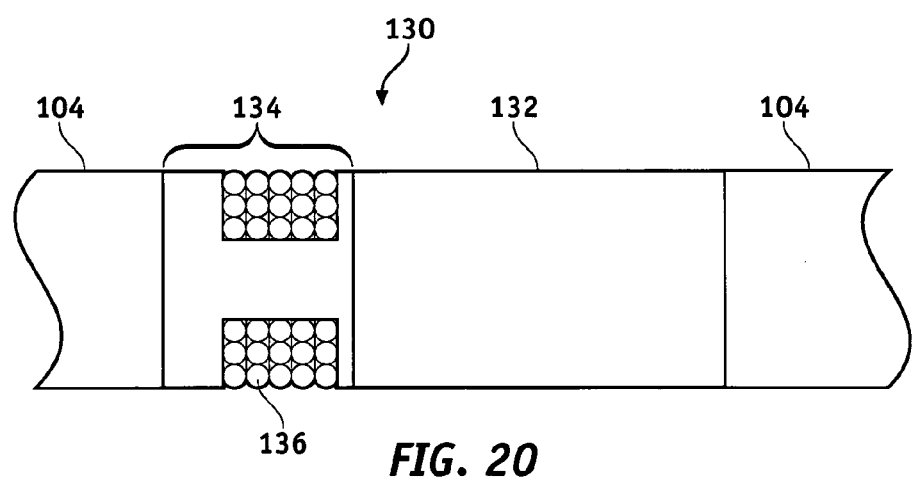
Figure 21:
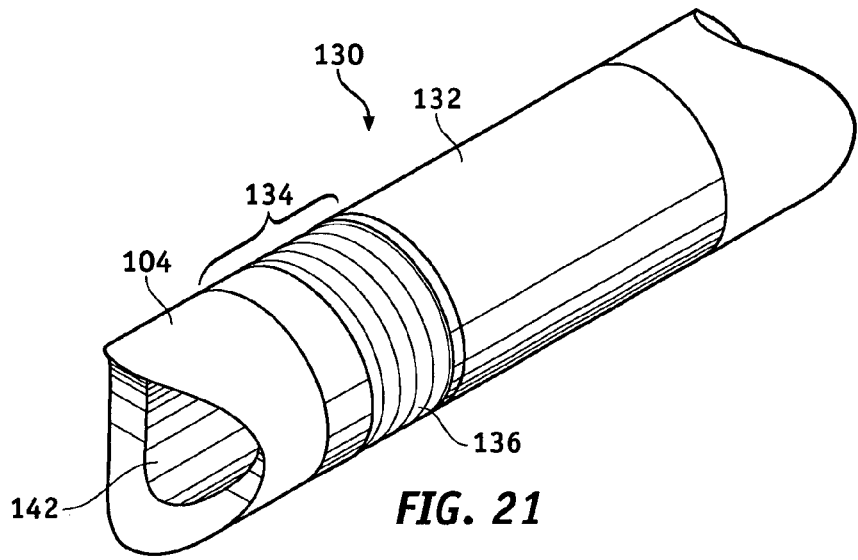
Figure 22:
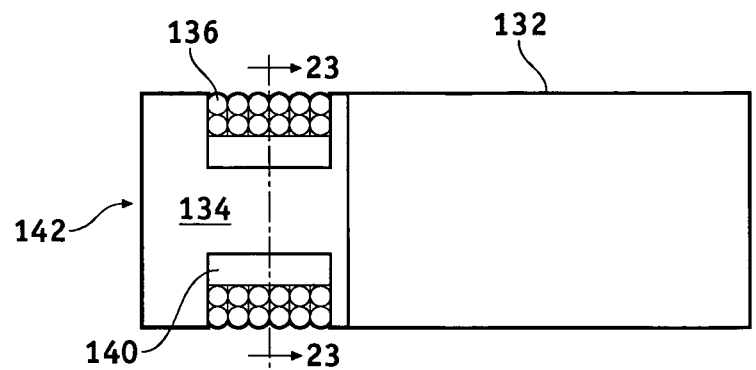
FIGS. 22 and 23 are side and cross-sectional views, respectively, of a bobbin in accordance with the present invention.
Figure 23:
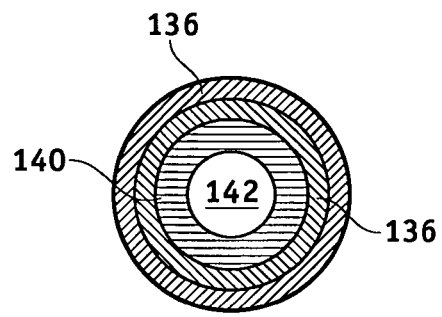

FIGS. 19, 20 and 21 are top, partial cross-sectional, and isometric views, respectively, of a stimulation lead 104 having a stimulation electrode/inductor assembly 130 configured thereon. An opening 142 is provided through which the filers (not shown) may pass. Stimulation electrode/inductor assembly 130 comprises an electrode body portion 132 and an integrated bobbin portion 134 around which are wound a plurality of coils of wire 136 forming an inductor. Wire 136 is insulated with, for example, a polymer such as urethane, polyamide, paralene, etc. In this manner, the inductor experiences little-to-no flexing, thus reducing the risk that the delicate coils of wire 136 will be broken. If desired, a ferrite core 140 may be provided to increase inductance as is shown in FIGS. 22 and 23. A suitable ferrite is one which does not saturate in an MRI environment (e.g. alloy 49 iron-nickel high permeability alloy).

It should be clear that the coils of wire 136 are not in contact with each other as a result of the above-mentioned insulation. To provide contact with body tissue, a portion of the insulation may be removed to expose the wire to the tissue. This may be accomplished in a number of ways; e.g. laser ablation, chemical etching, mechanical grinding, or if silicone insulation is applied, merely wiping off the silicone before it cures. The result is that the wire coils are insulated from each other, but the outer coils are in contact with body tissue.

Figure 24:
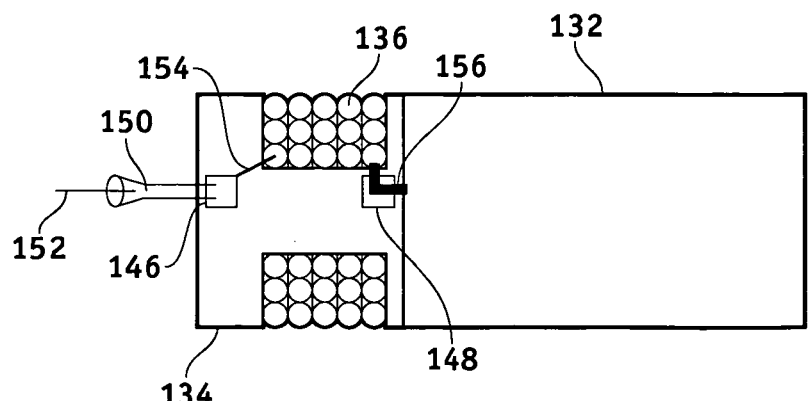
FIG. 24 is a cross-sectional view of a bobbin equipped with integral bonding pads in accordance with the present invention.

In FIG. 24, bobbin portion 134 includes integral bonding pads 146 and 148. The coil is electrically coupled to stimulation electrode 132 by means of bonding pad 148 as is shown at 156. The coil is also electrically coupled to bonding pad 146 as is shown at 154. Therefore, electrically coupling filer 152, as for example by means of a crimping sleeve 150 coupled to bonding pad 146, places the inductor in the stimulation path between filer 152 and stimulation electrode 132. The connections of the coil wire and crimp sleeve to the bonding pads may be accomplished by any of a number of known techniques; e.g. soldering, welding, etc. The wire may be comprised of MP35n (a chromium-cobalt alloy), platinum, platinum-indium, or other biocompatible metal.

If sufficient inductance cannot be obtained with a single layer of windings, multiple layers of windings may be utilized as already shown in FIGS. 19-24. This could be realized by using a wire that has an insulated portion and an uninsulated portion. The insulated portion makes up the lower layers of windings, and the uninsulated portion makes up the outer layer of windings. The insulated portion provides the requisite inductance, and the uninsulated portion provides for electrical coupling to the patient's tissue.

Figure 25:
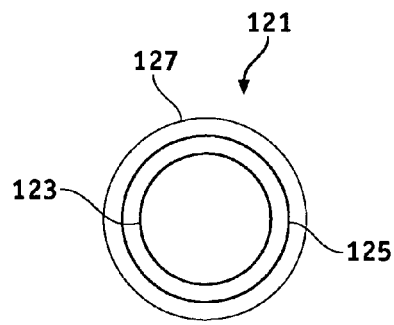
FIGS. 25 and 26 are cross-sectional and side views of an integrated choke/electrode in accordance with the invention.
Figure 26:
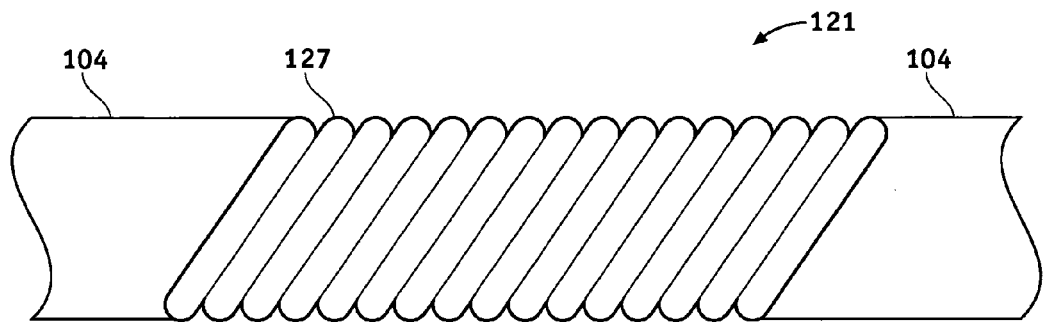

An integrated choke/electrode of the type described above is shown in FIGS. 25 and 26 which are cross-sectional and side views of an integrated choke/electrode assembly 121 in accordance with the present invention. Referring to FIG. 25, the windings are constructed from a wire having a first portion which is insulated and a second portion which is uninsulated. Inner layers of windings 123 and 125 are made from the insulated portion as is shown in FIG. 25. Outer layer of windings 127 is made from the uninsulated portion of the wire as is shown in FIGS. 25 and 26.

Figure 27:
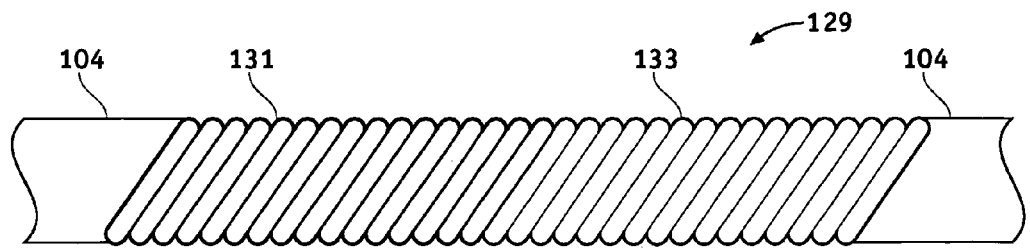
FIG. 27 is a side view of another integrated/choke assembly in accordance with the invention.

FIG. 27 is a side view of another choke/electrode assembly 129. An insulated portion 131 of a wire is helically wound and acts as a choke. The uninsulated portion 133 acts as a stimulation electrode.

Figure 28:
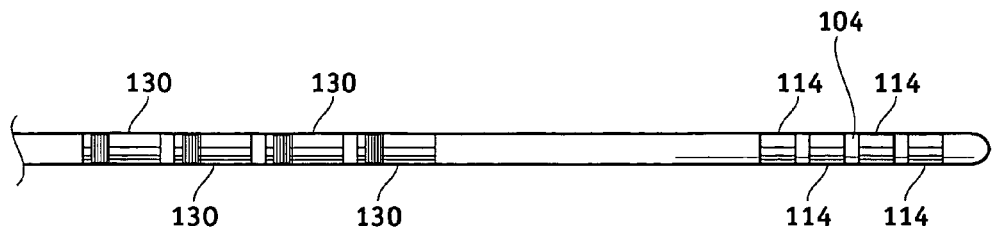
FIG. 28 is a side view illustrating yet another embodiment of the present invention.

FIG. 28 is a side view illustrating a further embodiment of the present invention. As previously described, the distal end of electrode 104 is provided with a plurality of stimulation electrodes 114, each of which is electrically associated with a different inductor/bobbin assembly 130. In this case, the inductor/bobbin assemblies 13 are not attached to the stimulation electrodes 114, but are each placed in the stimulation path associated with one of the stimulation electrodes. The coil terminals may be electrically coupled into the filer path using, for example, bonding pads on each bobbin as previously described. In this embodiment, the length of each bobbin may be sufficient to warrant using a flexible material to make the bobbins so as to avoid compromising the flexibility of the lead.

Figure 29:
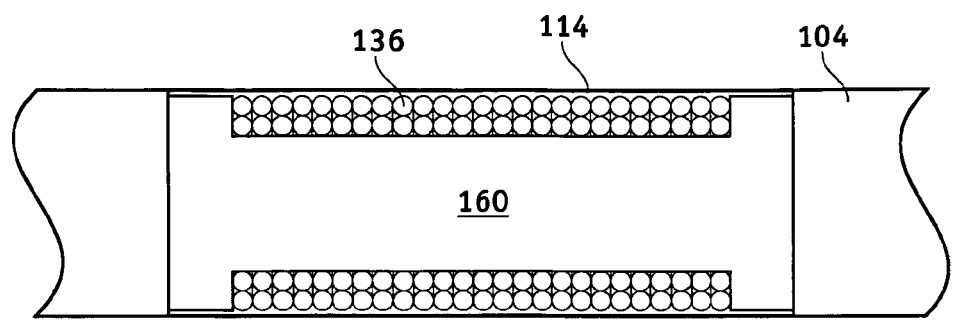
FIG. 29 is a cross-sectional view of yet another embodiment of the present invention.

To more fully protect the windings of the wire from possible damage, the inductor could be placed inside the stimulation electrode. For example, a coil could be wound on a bobbin 160 as shown in FIG. 29, and the wound bobbin placed partially or entirely inside an electrode 114 as illustrated. This arrangement has an additional advantage in that a capacitance (and therefore a capacitive, frequency-dependant impedance) is achieved as a result of the spatial relationship between the coils 136 of the inductor and the stimulation electrode 114. This capacitance will be further discussed below. An alternative arrangement involves the use of a flex circuit having traces provided thereon which may be rolled and placed inside the stimulation electrode.

Figure 30:
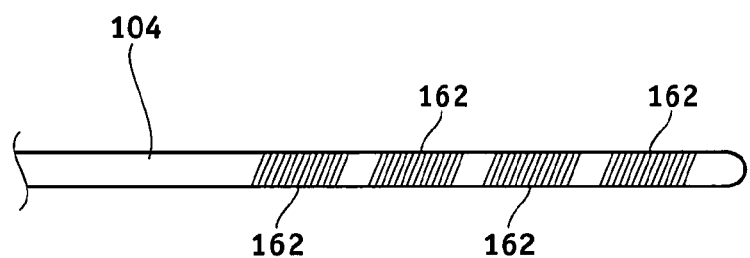
FIG. 30 is a side view of a further embodiment of the present invention wherein the stimulation electrodes are themselves shaped as coils.

FIG. 30 is a side view of a still further embodiment of the present invention. In this embodiment, stimulation electrodes 162 are provided which are themselves configured as coils in order to provide the requisite frequency dependent impedance.

Of course, there are numerous other ways to manufacture coils. For example, wire could be wound on a cylindrical bobbin, and the bobbin subsequently removed. If the wire is wound on a spool-shaped bobbin of the type that has larger diameter end sections, these end sections could be broken or cut off and the coil removed. Alternatively, a coil could be masked and etched on a bobbin using electrochemical etching, or a film of metal could be deposited and the coil formed by machining.

Figure 31:
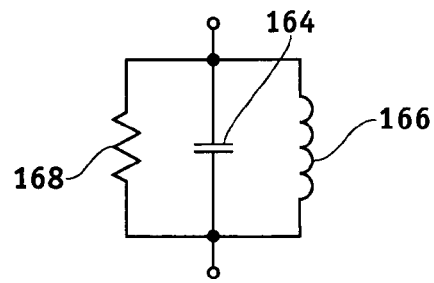
FIG. 31 is a schematic diagram of a parallel resonant circuit.

Another approach to providing the required frequency dependent impedance is to provide a resonant circuit that resonates at MRI frequencies (e.g. 64 MHz) and thus has significantly higher impedance at the higher MRI frequencies than it does at the lower stimulation frequencies, thus increasing the effectiveness of the inductor at MRI frequencies. To accomplish this, a capacitance (shown at 164 in FIG. 31) is added to the system in parallel with inductor 166. Resistor 168, in parallel with capacitor 164 and inductor 168, completes the resonant circuit.

The resonant frequency is governed by:

$$f = \frac{1}{2\pi\sqrt{LC}} \quad \text{Equation (4)}$$

where f is the resonant frequency, L is the inductance, and C is the capacitance. If resistance is added to the system, the bandwidth of the impedance can be increased. The quality factor of the circuit impacts the bandwidth and for a parallel resonant circuit is defined by:

$$Q = 2\pi RC \quad \text{Equation (5)}$$

where Q is the quality factor, R is the resistance, and C is the capacitance. The impedance of a parallel resonant circuit as a function of frequency is:

$$Z(j\omega) = R\frac{j(\omega/\omega_o)}{Q[1-(\omega/\omega_o)^2]+j(\omega/\omega_o)} \quad \text{Equation (6)}$$

Where $\omega_o = 2\pi f_o$ and $f_o$ is the resonant frequency

Figure 32:
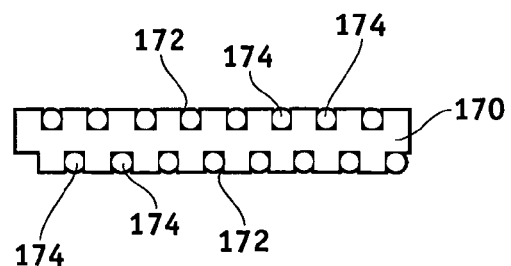
FIG. 32 is a side view of yet another embodiment of the present invention.

Capacitor 164 may comprise one or more discrete capacitors as is well known. It is also known however, that capacitance exists between the windings of an inductor and is sufficient to create a resonant circuit at a predetermined frequency if properly controlled. The control required to insure that the proper capacitance between inductor windings may be provided by the bobbin arrangement shown in FIG. 32 which is a cross-sectional view of bobbin 170 that is provided with one or more grooves 172 (e.g. a helical groove) for receiving and positioning inductor winding 174. Capacitance may be controlled by properly choosing the spacing between grooves 172, which may extend partially or completely around the periphery of the bobbin. The capacitance can also be adjusted by providing a predetermined number of layers of windings or by varying the thickness of the insulation. Utilizing the methods described above, the resulting inductor may then be positioned in the stimulation path, either outside the stimulation lead or partially or completely within the stimulation lead.

The inductance of each filer can be increased and an RF choke created as shown in FIG. 33. That is, each filer 176 is passed through a ferrite bead 178. By passing the filer through the ferrite bead more than once as shown in FIG. 34, the inductance is further increased.

FIG. 35 is an isometric view of another embodiment of the present invention. An insulated wire 180 is wound around a metallic tube 182 forming coils 136 therearound. Tube 182 resides within electrode 114. Wire 180 is electrically coupled (e.g. by spot welding, laser welding, etc.) to tube 182 as is shown at 184 and to electrode 114 as is shown at 186. Inner tube 182 is provided with a connector 188 that may be used to electrically couple filer or filer cable 152 to inner tube 182 as, for example, by crimping or welding. Thus, an inductor has been implemented in series between filer 152 and electrode 114.

FIG. 36 is an isometric view of yet another embodiment of the present invention. As was the case in FIG. 35, an inner metallic tube 182 resides within electrode 114, and an insulated wire 180 is wound around tube 182 forming the coils 136 of an inductor having one end electrically coupled at 190 to electrode 114 as, for example, by welding. In this embodiment, however, a longitudinal groove 192 is provided in inner tube 182, and a conductive connector tube 194 resides generally within groove 192. Inductor wire 180 is electrically coupled to the distal end of tube 194 as, for example, by crimping as is shown at 198, and filer 152 is electrically coupled to a proximal end of tube 194 as, for example, by crimping as is shown at 200. In this manner, an inductor including coils 136 has been placed in series with filer 152 and electrode 114.

While at least one exemplary embodiment has been presented in the foregoing detailed description of the invention, it should be appreciated that a vast number of variations exist. For example, while the invention has been described in connection with neurostimulation systems, the invention is equally applicable to other lead assemblies (e.g. implantable cardiac leads) that may be adversely impacted in high frequency environments such as is encountered during an MRI scan. It should also be appreciated that the exemplary embodiment or exemplary embodiments are only examples, and are not intended to limit the scope, applicability, or configuration of the invention in any way. For example, while distal electrodes 114 have been referred to as stimulation electrodes used to deliver therapy to a patient's body tissue, it should be clear to one skilled in the art that electrodes 114 could also be used for sensing. Additionally, while only inductors having substantially circular cross-sections have been shown and described, it should be clear that inductors having other than circular (e.g. oval, flattened, rectangular, etc.) cross-sections are considered to be well within the scope of the invention. For example, an oval, somewhat flattened inductor might be especially suitable in the case of a paddle-lead.

The foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims.

What is claimed is:

1. A pulse stimulation system for implantation into a patient's body, the system comprising:
   a pulse generator having a stimulation pulse output;
   a lead body;
   a conductive filer positioned within said lead body and having a proximal end directly electrically coupled to said stimulation pulse output of said pulse generator and having a distal end region; and an electrode coupled to said lead body, said electrode comprising:

a stimulation portion;

a bobbin; and a wire wound on said bobbin and having a first end and a second end, the wire forming an inductor between said distal end region and said stimulation portion, wherein said inductor is positioned at least partially within said stimulation portion and wherein said bobbin comprises:

a first conductive tube at least partially within said stimulation portion, said conductive tube having a longitudinal groove therein; and a second conductive tube having a proximal end and a distal end positioned within said groove between said conductive tube and said wire, said wire having a first end electrically coupled to said stimulation portion and a second end electrically coupled to said distal end of said second conductive tube, and said distal end region of said filer electrically coupled to said proximal end of said second conductive tube.

2. A pulse stimulation system according to claim 1 wherein said inductor comprises a crimping sleeve electrically connected between the distal end region and a first end of the at least one wire.

3. A pulse stimulation system according to claim 2 wherein said bobbin comprises at least one groove therein for receiving and positioning said wire.

4. A pulse stimulation system according to claim 3 wherein said inductor comprises a plurality of coils of wire and wherein said bobbin comprises a plurality of grooves therein for receiving and positioning said wire to achieve a desired capacitance.

5. A pulse stimulation system according to claim 4 wherein said inductor is configured to interact with said capacitance to form a resonant circuit.

6. A pulse stimulation system according to claim 2 wherein said bobbin further comprises a ferrite core around which said wire is wound.

7. A pulse stimulation system according to claim 1 wherein said inductor is positioned substantially completely within said stimulation portion.

8. The pulse stimulation system of claim 1, wherein said inductor comprises a plurality of coils of wire and wherein said bobbin comprises a plurality of grooves therein for receiving and positioning said wire to achieve a desired capacitance by spacing apart each turn of the wire.

9. A pulse stimulation system for implantation into a patient's body, the system comprising:

a pulse generator;

a lead body;

a conductive filer positioned within said lead body and having a proximal end electrically coupled to said pulse generator and having a distal end region; and an electrode coupled to said lead body, said electrode comprising:

a stimulation portion;

a bobbin; and a wire wound on said bobbin and having a first end and a second end, the wire forming an inductor between said distal end region and said stimulation portion, wherein said inductor is positioned at least partially within said stimulation portion and wherein said bobbin comprises:

a first conductive tube at least partially within said stimulation portion, said first conductive tube having a longitudinal groove therein; and a second conductive tube having a proximal end and a distal end positioned within said groove between said first conductive tube and said wire, said wire having a first end electrically coupled to said stimulation portion and a second end electrically coupled to said distal end of the second conductive tube, and said distal end region of said filer electrically coupled to said proximal end of the second conductive tube.

10. The pulse stimulation system of claim 9, wherein said inductor is positioned at least partially within said stimulation portion and wherein the pulse generator has a stimulation pulse output and wherein the conductive filer is directly electrically coupled to said stimulation pulse output of said pulse generator.

* * * * *